US011564865B2

(12) United States Patent
Altrichter et al.

(10) Patent No.: US 11,564,865 B2
(45) Date of Patent: *Jan. 31, 2023

(54) MEANS AND METHODS OF STERILIZATION OF BIOFUNCTIONAL COMPOSITIONS

(71) Applicant: Leukocare AG, Munich (DE)

(72) Inventors: Jens Altrichter, Kavelstorf (DE); Anja Breuer, Babenhausen (DE); Nicole Schaath, Frankfurt (DE); Julia Quathamer, Obertshausen (DE)

(73) Assignee: Leukocare AG, Martinsried (DE)

( * ) Notice: Subject to any disclaimer, the term of this patent is extended or adjusted under 35 U.S.C. 154(b) by 397 days.

This patent is subject to a terminal disclaimer.

(21) Appl. No.: 14/157,381

(22) Filed: Jan. 16, 2014

(65) Prior Publication Data

US 2014/0134214 A1 May 15, 2014

Related U.S. Application Data

(63) Continuation of application No. 13/262,387, filed as application No. PCT/EP2010/054390 on Mar. 31, 2010, now Pat. No. 8,685,459.

(30) Foreign Application Priority Data

Mar. 31, 2009 (EP) .................................. 09004735

(51) Int. Cl.
*A61J 1/00* (2006.01)
*C12Q 1/22* (2006.01)
*G01N 33/543* (2006.01)

(52) U.S. Cl.
CPC .................................. *A61J 1/00* (2013.01); *C12Q 1/22* (2013.01); *G01N 33/54393* (2013.01)

(58) Field of Classification Search
CPC ........ A61J 1/00; C12Q 1/22; G01N 33/54393
See application file for complete search history.

(56) References Cited

U.S. PATENT DOCUMENTS

| 3,051,627 | A | * | 8/1962 | Bradford | C12N 9/96 435/188 |
| 3,957,049 | A | * | 5/1976 | Neefe | A61F 9/0017 351/159.04 |
| 4,121,588 | A | * | 10/1978 | Geiger | 604/110 |
| 4,244,943 | A | | 1/1981 | Yamahira et al. | |
| 4,328,182 | A | * | 5/1982 | Blake | G01N 31/226 116/206 |
| 5,730,933 | A | | 3/1998 | Peterson | |
| 6,140,127 | A | * | 10/2000 | Sprague | A61L 31/047 424/423 |
| 6,203,791 | B1 | * | 3/2001 | Protopapa | A61Q 9/04 424/94.64 |
| 8,685,459 | B2 | * | 4/2014 | Altrichter | G01N 33/54393 424/489 |
| 8,961,984 | B2 | * | 2/2015 | Irvin | A61B 5/14546 424/185.1 |
| 9,797,895 | B2 | * | 10/2017 | Margraf | G01N 33/54393 |
| 2002/0077277 | A1 | * | 6/2002 | Usala | 514/2 |
| 2008/0023345 | A1 | * | 1/2008 | Vonderwalde | A45C 11/005 206/5.1 |
| 2008/0044553 | A1 | * | 2/2008 | Freeman | A61L 2/07 427/2.24 |
| 2009/0074749 | A1 | | 3/2009 | Chtourou et al. | |
| 2012/0093803 | A1 | | 4/2012 | Altrichter et al. | |

FOREIGN PATENT DOCUMENTS

| EP | 0805353 A | 11/1997 | |
| EP | 1571204 A1 | 9/2005 | |
| JP | 60-120823 | 6/1985 | |
| JP | 11-199511 | 7/1999 | |
| JP | 2003-527210 A | 9/2003 | |
| JP | 2003300908 A | * 10/2003 | |
| JP | 2004-532068 A | 10/2004 | |
| JP | 2008-545461 A | 12/2008 | |
| WO | WO-9423767 A1 | * 10/1994 | ........... A61K 31/727 |
| WO | WO2001012797 A2 | 2/2001 | |
| WO | 01/70279 A1 | 9/2001 | |
| WO | 02/082462 A2 | 10/2002 | |
| WO | 02/082462 A3 | 10/2002 | |
| WO | WO-03020329 A1 | * 3/2003 | ........... A61K 31/404 |
| WO | 03/026705 A1 | 4/2003 | |
| WO | 03/030949 A1 | 4/2003 | |

(Continued)

OTHER PUBLICATIONS

The 28th Conference on Pharmaceutical Technology, Academy of Pharmaceutical Science and Technology, Japan, 2003.
Anderson et al., "Characterizing Ionic Liquids On the Basis of Multiple Solvation Interactions," J. Am Chem. Soc., 124(47):14247-24254, 2002.
Baker et al., "An analytical view of ionic liquids," Analyst, 130:800-808, 2005.
Branco et al., "Highly Selective Transport of Organic Compounds by Using Supported Liquid Membranes Based on Ionic Liquids," Angew. Chem. Int. Ed., 41(15):2771-2773, 2002.
Branco et al., "Studies on the Selective Transport of Organic Compounds by Using Ionic Liquids as Novel Supported Liquid Membranes," Chem. Eng. J., 8(17):3865-3871, 2002.

(Continued)

*Primary Examiner* — Ali Soroush
(74) *Attorney, Agent, or Firm* — Lee & Hayes, P.C.

(57) ABSTRACT

The present invention, inter alia, relates to a closed sterilized container comprising at least one carrier which is a stabilizer; and at least one biomolecule reversibly attached to the carrier, wherein said carrier partially or completely covers the attached biomolecules and wherein said at least one carrier is selected from the group consisting of (poly) peptides such as dipeptides or tripeptides, amino acids, polyalcohols, polyethyleneglycols, ionic liquids, compatible solutes, saponins and a mixture thereof. The invention also relates to methods for producing sterilized containers according to the invention and uses thereof.

13 Claims, 19 Drawing Sheets

(56) References Cited

FOREIGN PATENT DOCUMENTS

Figure 1:
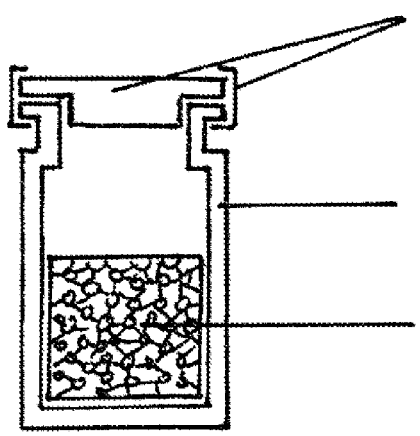
Figure 2:
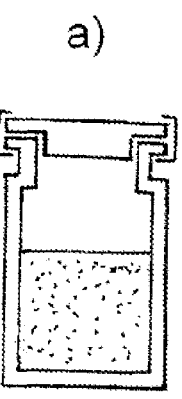
Figure 2:
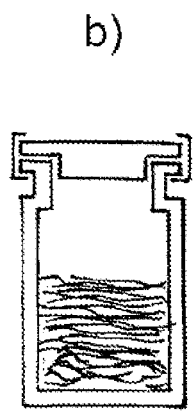
Figure 2:
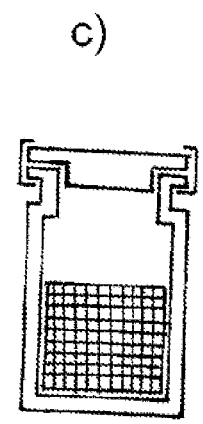
Figure 2:
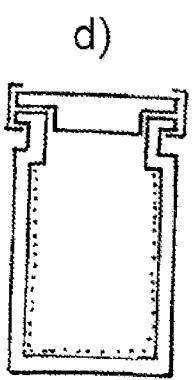
Figure 2:
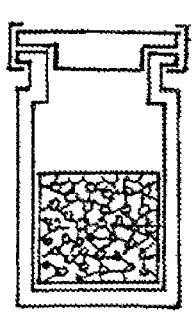
Figure 2:
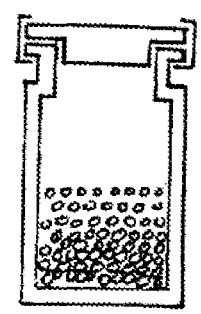
Figure 2:
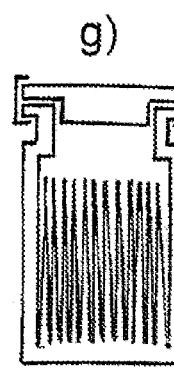

| WO | WO2004032980 | A1 | 4/2004 |
|----|----|----|----|
| WO | WO2006087205 | A1 | 8/2006 |
| WO | 2006/124988 | A2 | 11/2006 |
| WO | 2006/124988 | A3 | 11/2006 |
| WO | 2006/130869 | A1 | 12/2006 |
| WO | 2007/077365 | A2 | 7/2007 |
| WO | 2007/128550 | A | 11/2007 |
| WO | 2007/128550 | A1 | 11/2007 |

OTHER PUBLICATIONS

Chen et al., "Enhancement of tolerance of abiotic stress by metabolic engineering of betaines and other compatible solutes," Current Opinion in Plant Biology, 5:250-257, 2002.

Empadinhas et al., "Diversity and biosynthesis of compatible solutes in hyper/thermophiles," Inter. Microbiol. 9:199-206, 2006.

Van Der Kooij, M, Office Action issued in European Patent Application No. 10712939.7, European Patent Office, dated May 15, 2014.

Eidel, Clemence, International Search Report and Written Opinion, PCT/EP10/54390, European Patent Office, dated Jun. 29, 2010.

Soroush, Ali, Non-Final Office Action, United States Patent & Trademark Office, U.S. Appl. No. 13/262,387, filed Mar. 12, 2013.

Soroush, Ali, Notice of Allowance/Reasons for Allowance, United States Patent & Trademark Office, U.S. Appl. No. 13/262,387, filed Sep. 27, 2013.

EP Office Action dated Apr. 8, 2015 in European Patent Application No. 10712939.7, 8 pages.

European Search Report dated Oct. 16, 2009 in European Application No. 09004735.8, 8 pages.

European Search Report dated Nov. 28, 2016 in European Application No. 16176458, 6 pages.

European Search Report dated Apr. 8, 2013 in European Application No. 10712939.7, 8 pages.

Priorix-Tetra, Technical Information, Approved Jul. 2006. downloaded May 2, 2022 from https://gskpro.com/de-de/produkte/priorix-tetra/, 12 pages.

\* cited by examiner

Lid (e.g. srew cap or rubber stopper with crimp)

Container
(e.g. vial / phial / ampulla)

Carrier
(e.g. open porous foam)

a) 
b) 
c)

d) 
e) 
f)

g)

EGS (Ethylene glycol bis[succinimidylsuccinate])

BSOCOES (Bis[2-(succinimidooxycarbonyloxy)ethyl]sulfone)

DSP (Dithiobis[succinimidylpropionate])

DST (Disuccinimidyl tartarate)

Succinimidyl 2-([4,4'-azipentanamido]ethyl)- 1,3'- dithioprionate

Sulfosuccinimidyl-2-(*m*-azido-*o*-nitrobenzamido)-ethyl-1,3'-proprionate

MEANS AND METHODS OF STERILIZATION OF BIOFUNCTIONAL COMPOSITIONS

CROSS REFERENCE TO RELATED APPLICATION

This application is a continuation of U.S. application Ser. No. 13/262,387 having a filing date of Nov. 25, 2011, which is a U.S. National Stage Application filed under 35 U.S.C. § 371 based upon International Application No. PCT/EP2010/054390, filed Mar. 31, 2010, which application claims priority to European Application No. 09004735.8, filed Mar. 31, 2009, the disclosures of which are incorporated herein by reference in their entirety.

TECHNICAL FIELD

The present invention, inter alia, relates to a closed sterilized container comprising at least one carrier which is a stabilizer; and at least one biomolecule reversibly attached to the carrier, wherein said carrier partially or completely covers the attached biomolecules and wherein said at least one carrier is selected from the group consisting of (poly) peptides such as dipeptides or tripeptides, amino acids, polyalcohols, polyethyleneglycols, ionic liquids, compatible solutes, saponins and a mixture thereof. The invention also relates to methods for producing sterilized containers according to the invention and uses thereof.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

STATE OF THE ART

A major concern in the manufacturing of therapeutic and prophylactic products is to assure that no microbial contaminants can be transmitted to the recipient or user of such products. However, these pharmaceutical products are generally sourced from biological materials which may contain pathogens like e.g. viruses or their manufacturing process makes use of reagents or culture media that are suspicious to be contaminated with pathogens.

International guidelines therefore recommend to introduce in the manufacturing process of pharmaceuticals dedicated steps to remove or inactivate those potential bacterial or viral contaminants. The European Note for Guidance CPMP/BWB/268/95 of 14 February 1996 defines what is a clearly effective method for inactivating or removing viruses as a method which is able to reduce infectivity by about 4 Log (=4 log 10) or more.

Numerous methods exist for the removal or inactivation of viruses and other contaminants, e.g. ethylene oxide treatment, solvent-detergent (SD) treatment, heat or acid pH treatment, chromatography, nanofiltration, pasteurization or irradiation.

However, all of these methods suffer from severe drawbacks:

Ethylene oxide treatment has the disadvantage that it often reacts with proteins. In addition, because of the known tissue toxicity and carcinogenic potential of the by-products of ethylene, it is only allowed to add very small amounts of ethylene oxide to biopharmaceuticals.

WO 97/42980 describes a sterilization method of biologically active compounds which uses heat inactivation. The method includes obtaining a dried sample containing an amount of trehalose sufficient to render heat stability and exposing the dried sample to heating conditions at a temperature and for a duration sufficient to substantially inactivate viruses. However, the time and temperature applied does not comply with the definition of sterilization. Sterilization is defined as a validated process for the removal or destruction of all forms of microbial life (bacteria, viruses, fungi, spores) (WHO Aids Series No. 2, second edition. Guidelines on sterilization and disinfection methods' effective against human immunodeficiency virus (HIV). Geneva: World Health Organization, 1989). Because for statistical reasons the complete removal can not being proofed during validation. Therefore, the term "sterility assurance level" (SAL) is used as measure of sterility. According to ISO 11139: 2006 (1) Sterility Assurance Level (SAL) is the probability of a single viable microorganism occurring on an item after sterilization. The term SAL takes a quantitative value, generally $10^{-6}$ or $10^{-3}$. When applying this quantitative value to assurance of sterility, an SAL of $10^{-6}$ takes a lower value but provides a greater assurance of sterility than an SAL of $10^{-3}$. A SAL of $10^{-6}$ means that there is a chance of less than 1 in a million ($10^{-6}$) that a particular item is contaminated. SAL=$10^{-6}$ is the acceptable standard for critical items. To assure an SAL=$10^{-6}$ by dry heat sterilization time and temperature are important. The following time and temperature combinations are generally accepted that have to be exceeded to assure a SAL=$10^{-6}$:

60 min at 170° C. (340° F.)
120 min at 160° C. (320° F.)
150 min at 150° C. (300° F.)
12 hours at 121° C. (250° F.)

The method described in WO 97/42980 is not sufficient to assure a SAL=$10^{-6}$. Therefore, the term "sterilisation" is misused and the method is rather a "virus reduction method" than a sterilisation method.

U.S. Pat. No. 5,730,933 discloses a method for the inactivation of bio-functional compounds using radiation sterilization. Radiation sterilization has the advantage of high penetrating ability, relatively low chemical reactivity and instantaneous effect without the need to control temperature, pressure, vacuum or humidity. Furthermore, radiation sterilization is widely used in industry for a variety of products and both dosage levels and its biological effects are well known. In general a radiation dose of >25 kGy has proven to assure a SAL=$10^{-6}$ during validation of sterilisation procedures.

The radiation sterilization method disclosed in U.S. Pat. No. 5,730,933 involves the incubation of the biological compound in a protection solution which contains proteins (gelatine, bovine serum albumin) and free radical scavengers as well as the freezing of the biological compounds. While freezing of biologically active compounds is an essential part of method disclosed in U.S. Pat. No. 5,730,933 it has the disadvantage that the activity of the bio-functional compound is drastically reduced, in the examples cited in U.S. Pat. No. 5,730,933 to less than 10 percent of the activity before sterilization and freezing. Furthermore, protein-containing solutions like the one used in U.S. Pat. No. 5,730,933 have the disadvantage that the bio-functional compounds that are incubated in these solutions have a high risk of being contaminated by micro-organisms.

Another solution to produce non-contaminated pharmaceuticals is their aseptic production. However, a major drawback of this approach is that the whole production process has to be performed under aseptic conditions in a clean room. This is time consuming and cost intensive. In addition, only low security level can be reached by aseptic production. Usually, an aseptic production is able to assure only a SAL=$10^{-3}$, meaning that the process is validated to assure that less than 1 in thousand particular items produced under aseptic conditions are free of microbial contaminations. This is a thousand times less than regular sterilization.

Thus, there is a need of providing sterilization methods that are compatible with the manufacturing of biopharmaceuticals.

A major challenge when sterilizing bio-functional compounds is to avoid irreversible changes to active compounds during sterilization. Therapeutic proteins are in general of complex structure and quite fragile, i.e. sensitive to degradation (modification of their primary structure) and/or denaturation (modification of their secondary, tertiary and quaternary structures, which makes them difficult to withstand aggressive virus inactivation or sterilization methods.

These molecular modifications after sterilization may result in a loss of the biological activity or antigenic properties of these compounds, in a reduced stability in their pharmaceutical form upon storage and in new immunogenicity properties which might put the recipient of such products at risk of allergic reactions upon repeated administration or application.

SUMMARY OF THE INVENTION

The invention relates to a sterile container, comprising a carrier, at least one biomolecule reversibly attached to the carrier, at least one stabilizer which partially or completely covers the attached biomolecules; and optionally a lid, wherein said at least one stabilizer is selected from the group consisting of (poly)peptides, amino acids, carbohydrates, polyalcohols, polyethyleneglycols, ionic liquids, compatible solutes, saponins and a mixture thereof; as well as to other embodiments as characterized in the claims.

In addition, the present invention relates to a closed sterilized container comprising at least one carrier which is a stabilizer; and at least one biomolecule reversibly attached to the carrier, wherein said carrier partially or completely covers the attached biomolecules and wherein said at least one carrier is selected from the group consisting of (poly)peptides such as dipeptides or tripeptides, amino acids, polyalcohols, polyethyleneglycols, ionic liquids, compatible solutes, saponins and a mixture thereof.

Surprisingly, it was found that by providing biomolecules in a container according to the invention or producible or produced according to the method of the present invention, the following advantages over the state of the art are achieved:

The biomolecules comprised in the containers of the present invention retain a very high degree of their activity even after standard sterilization methods that are known to result in a SAL of $10^{-6}$. Therefore, the containers comprising the biomolecule can be filled and closed before sterilization and can be sterilized, preferably terminally or bulk sterilized. The (terminal or bulk) sterilization allows the production of the biomolecule-comprising container under non-sterile or semi-sterile conditions. Due to this feature, the production costs can be greatly reduced compared to the costs for the production of conventional containers for biomolecules that have to be produced under i.e. aseptic conditions.

The sterilized containers which have been (terminally or bulk) sterilized obtained in such a way contain stable biofunctional products that do not contain measurable pathogens, i.e. no or essentially no viable pathogens, or inactivated pathogens or an amount of pathogens which is not detectable that retain a significant percentage of their activity.

The invention furthermore relates to methods for producing sterilized containers.

The methods include obtaining a sample in a container containing a stabilizer in a sufficient amount to render stability to the bio-functional product and exposing the sample to sterilization conditions for a duration sufficient to substantially inactivate pathogens, especially bacteria and viruses. The sterilization conditions include ethylene oxide treatment, heat inactivation, autoclaving, plasma sterilization and, preferably, irradiation like beta or gamma irradiation.

No scavengers have to be added during the sterilization procedure.

Due to the introduction of stabilizers most biomolecules can even be stored at room temperature for long times.

Because of the reversible attachment of the biomolecules onto the carrier in the container, a fast release of the biomolecules after addition of a suitable solvent is achieved. This enables for the direct use of the biomolecule-containing solution for the injection into a patient.

DETAILED DESCRIPTION OF THE INVENTION

In a first embodiment, the present invention provides a sterile container comprising a carrier, at least one biomolecule reversibly attached to the carrier, at least one stabilizer that covers the biomolecule(s) partially or completely and optionally a lid, wherein said at least one stabilizer is selected from the group consisting of (poly)peptides, amino acids, carbohydrates, polyalcohols, polyethyleneglycols, ionic liquids, compatible solutes, saponins and a mixture thereof, wherein preferably the stabilizer itself is the carrier.

The present invention provides a closed sterilized container comprising at least one carrier which is a stabilizer; and at least one biomolecule reversibly attached to the carrier, wherein said carrier partially or completely covers the attached biomolecules and wherein said at least one carrier is selected from the group consisting of (poly)peptides such as dipeptides or tripeptides, amino acids, polyalcohols, polyethyleneglycols, ionic liquids, compatible solutes, saponins and a mixture thereof.

The term 'container' in the context of the present invention refers to all suitable receptacles for biomolecules. These receptacles can be selected, but are not limited, to vials, ampulla, cryocontainers, tubes, phials, flasks, bottles and bags.

The container and the lid (when the container comprises a lid) can be formed by separate elements (e.g. glass vial with rubber stopper) or be prepared in one piece (e.g. plastic ampulla).

The term "at least one" in connection with the terms "biomolecule", "carrier" and "stabilizer" relates to the presence of at least one kind of molecule such as at least one kind of biomolecule and/or at least one kind of stabilizer. The term does not relate to the number of molecules.

The term 'biomolecules' describes in the context of the invention any material which is essentially of biological origin and which has characteristics that are relevant for pharmaceutical, diagnostic and scientific applications. Biomolecules are organic molecules that are preferably produced by a living organism, including, preferably biodegradable, polymeric molecules such as (poly)peptides or peptides, carbohydrates lipids and fatty acids and nucleic acids as well as small molecules such as primary metabolites, secondary metabolites, and natural products. Other preferred biomolecules are combinations of the above molecules, e.g. glycoproteins, proteoglycans, glycolipids, nucleic acid-protein complexes. The term 'biomolecules' not only comprises native molecules as they can be isolated from natural origins but also (derivatives of) naturally occurring biomolecules or biologically active fragments thereof as well as artificial, recombinant or (semi)synthetic molecules, i. e. naturally occurring or artificial molecules which are produced synthetically, semisynthetically or recombinantly. Artificial molecules are e. g. those derived from naturally occurring molecules with alterations introduced. Biodegradable polymeric molecules other than those belonging to the above-mentioned classes are lignin and polyhydroxylalcanoates (natural polymers) and polyalcylene esters, polylactic acid and its copolymers, polyamide esters, polyvinyl esters, polyvinyl alcohols and polyanhydrids (artificial polymers). All of the above molecules or classes of molecules are falling within the term "biomolecules".

For the person skilled in the art, it is understood that the term 'biomolecules' as applied in the present invention also comprises biomolecules as described above which are comprised in or on structures such as eukaryotic or prokaryotic cells, tissues, viruses, as well as fragments thereof (e.g. organelles, membranes or capsids). The term 'biomolecule' in terms of the present invention also includes biomolecules which are comprised in or on stem cells or tumor cells as well as fragments thereof. In this embodiment of the present invention, the biomolecules can be attached to the solid carrier in isolated form or comprised in or on said eukaryotic or prokaryotic cells, tissues, viruses or fragments thereof. Alternatively, the structures comprising the biomolecules, preferably on their surface, may serve as carriers according to the present invention.

Preferred biomolecules exert properties which are relevant for pharmaceutical, diagnostic or scientific applications. In other words, the biomolecules applicable in the present invention preferably exert a biological activity which makes them useful and applicable as pharmaceutically active agent(s), diagnostic agent(s) and/or research tools.

The term '(poly)peptide' as used herein describes a group of molecules which comprise the group of peptides, as well as the group of polypeptides, the latter term being interchangeably used with the term "protein". The group of peptides consists of molecules up to 30 amino acids, the group of polypeptides consists of molecules with more than 30 amino acids. In accordance with the invention, the group of 'peptides' also describes fragments of proteins of a length of 30 amino acids or less. Polypeptides or peptides may further form dimers, trimers and higher oligomers, i.e. consisting of more than one polypeptide or peptide molecule. Polypeptide or peptide molecules forming such dimers, trimers etc. may be identical or non-identical. The corresponding higher order structures are, consequently, termed homo- or heterodimers, homo- or heterotrimers etc. The terms "polypeptide", "protein" and "peptide" also refer to naturally modified polypeptides/proteins and peptides, wherein the modification is effected e.g. by glycosylation, acetylation, phosphorylation and the like. Such modifications are well known in the art. Especially preferred (poly) peptides are antibodies or fragments thereof which retain their binding specificity, enzymes, receptors, membrane proteins, transport proteins, blood coagulation factors, hormones, cytokines or functional fragments thereof.

Preferred stabilizers falling within the term "peptide" are dipeptides and tripeptides. Accordingly, the at least one stabilizer which may be a carrier is preferably at least one di- and/or tripeptide. More preferably, the stabilizer comprises at least two (corresponding to at least two stabilizers or, where the stabilizer is the carrier, at least two carriers; to be transferred accordingly to the following numbers), at least three, at least four, at least five, at least six, at least seven, at least eight, at least nine or at least ten different di- and/or tripeptides. Exemplary dipeptides are glycylglutamine (Gly-Gln, displaying an enhanced stability as compared to glutamine alone), glycyltyrosine (Gly-Tyr), alanylglutamine (Ala-Gln, the latter two displaying an increased solubility in water as compared to tyrosine alone) and glycylglycine. Further naturally occurring dipeptides are Carnosine ((beta-alanyl-L-histidine), Anserine (beta-alanyl-N-methyl histidine), Homoanserine (N-(4-Aminobutyryl)-L-histidine), Kyotorphin (L-tyrosyl-L-arginine), Balenine (or ophidine) (beta-alanyl-N tau-methyl histidine), Glorin (N-propionyl-γ-L-glutamyl-L-ornithine-δ-lac ethyl ester) and Barettin (cyclo-[(6-bromo-8-en-tryptophan)-arginine]). Further artificial dipeptides are Aspartame (N-L-a-aspartyl-L-phenylalanine 1-methyl ester) and pseudoproline. Exemplary tripeptides are Glutathione (γ-glutamyl-cysteinyl-glycine) and its analogues ophthalmic acid (L-γ-glutamyl-L-α-aminobutyryl-glycine) and Norophthalmic acid (γ-glutamyl-alanyl-glycine). Further tripeptides are Isoleucine-Proline-Proline (IPP), Glypromate (gly-pro-glu), Thyrotropin-releasing hormone (TRH, thyroliberin or protirelin) (L-pyroglutamyl-L-histidinyl-L-prolinamide), Melanostatin (prolyl-leucyl-glycinamide), Leupeptin (N-acetyl-L-leucyl-L-leucyl-L-argininal) and Eisenin (pGlu-Gln-Ala-OH). It is preferred that the at least one tripeptide, and more preferred all tripeptides, used as a stabilizer, when used in connection with medical applications according to the invention (see below) do not exert any pharmacological properties. The composition according to this preferred embodiment of the invention preferably does not contain proteins or fragments of proteins which are not amino acids, dipeptides or tripeptides. Accordingly, in this preferred embodiment of the present invention, the composition does not contain proteins or fragments thereof consisting of more than three amino acids. Instead, the composition according to this embodiment preferably further comprises at least one amino acid, preferably at least two, more preferably at least three, even more preferably at least four, at least five, at least six, at least seven, at least eight, at least nine, at least ten different amino acids or more such as at least eleven, at least 12, at least 13, at least 14, at least 15, at least 16, at least 17, at least 18, at least 19 or at least 20 different amino acids.

The term "nucleic acid" or "nucleic acid molecule", in accordance with the present invention, includes DNA, such as cDNA or genomic DNA, and RNA such as antisense RNA or siRNA. Further included are nucleic acid mimicking molecules known in the art such as synthetic or semisynthetic derivatives of DNA or RNA and mixed polymers. Such nucleic acid mimicking molecules or nucleic acid derivatives include phosphorothioate nucleic acid, phosphoramidate nucleic acid, 2'-O-methoxyethyl ribonucleic acid, morpholino nucleic acid, hexitol nucleic acid (HNA), locked nucleic acid (LNA) and peptide nucleic acid (PNA) (see Braasch and Corey, Chem Biol 2001, 8: 1). LNA is an RNA derivative in which the ribose ring is constrained by a methylene linkage between the 2'-oxygen and the 4'-carbon. Nucleic acid molecules may contain additional non-natural or derivative nucleotide bases, as will be readily appreciated by those skilled in the art. Nucleic acid molecules further include ribozymes, aptamers, plasmids and chromosomes. Nucleic acid molecules may be used in accordance with the present invention in isolated form or in complex with other biomolecules such as proteins, e. g. histone proteins or proteins of the ribosome.

The term "carbohydrate" relates to an organic compound that is an aldehyde or ketone with a number of hydroxyl groups added, usually one on each carbon atom that is not part of the aldehyde or ketone functional group. Depending on the length of the molecule, carbohydrates are termed mono-, oligo- or polysaccharides. As soon as carbohydrates are bound to non-carbohydrate molecules, the resulting molecules are termed glycosides. Modified carbohydrates have for example N-acethylester, caboxyl- or sulfate-side chains and may contain glucuronic acid, iduronic acid, galactosamine, glucosamine. Exemplary carbohydrates are amylopectin, glycogen, starch, alpha- and beta-glucan, dextran, and glycosaminoglycans like hyaluronic acid, heparin, heparan sulfate, chondroitin sulfate and derivatives thereof such as glycosides.

Especially preferred proteins are antibodies or fragments thereof which retain their binding specificity. Antibodies applicable in the present invention can be, for example, polyclonal or monoclonal. The term "antibody" also comprises derivatives of antibodies which still retain their binding specificity. Fragments of antibodies comprise, inter alia, Fab fragments, F(ab')2 or Fv fragments. Techniques for the production of antibodies and fragments thereof are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1998. These antibodies can be used, for example, for immunoprecipitation of molecules of interest or for removing unwanted molecules from body liquids of a patient.

The term "antibody" also includes embodiments such as synthetic, chimeric, single chain (such as scFv) and humanized antibodies or derivatives or fragments thereof which still retain their binding specificity. Various procedures are known in the art and may be used for the production of such antibodies and/or fragments. Further, techniques described for the production of single chain antibodies can be adapted to produce single chain antibodies specifically binding to a molecule of interest or fragments thereof. Also, transgenic animals may be used to express humanized antibodies. Most preferably, the antibody is a monoclonal antibody. For the preparation of monoclonal antibodies, any technique that provides antibodies produced by continuous cell line cultures can be used. Examples for such techniques include the hybridoma technique (Köhler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of a biomolecule of interest (Schier, Human Antibodies Hybridomas 7 (1996), 97-105; Malmborg, J. Immunol. Methods 183 (1995), 7-13). It is also envisaged in the context of this invention that the term "antibody" comprises antibody constructs that may be expressed in cells, e.g. antibody constructs which may be transfected and/or transduced via, amongst others, viruses or plasmid vectors. Once the antibody or fragment thereof has been obtained, the antibody itself or the DNA encoding it can be sequenced providing for the information to recombinantly produce the antibody or fragment thereof in small or large scale. Methods of the production of a recombinant antibody are known to the person skilled in the art.

The antibody or derivative or fragment thereof can be further chemically modified as is well known in the art.

The antibody may be of any class of antibody. It is most preferred that the antibody is monoclonal and of the IgG, IgM or IgY class. IgY antibodies represent the analogs of IgG antibodies in chicken.

The stabilizers are selected from the group consisting of (poly)peptides such as dipeptides or tripeptides, amino acids, carbohydrates, polyalcohols, polyethyleneglycols, ionic liquids, compatible solutes, saponins or a mixture thereof. The same holds true for stabilizers being carriers for which also the following list of examples apply.

Preferably, the stabilizers are selected from albumins (e.g. human serum albumin, bovine serum albumin, ovalbumin, lactalbumin), heat shock proteins of the Hsp100/Clp-family, the Hsp90-family, the Hsp70-family, the Hsp60/GroEL-family and the small heat shock proteins (sHsps) General chaperones: BiP, GRP94, GRP170, Lectin chaperones: calnexin and calreticulin, non-classical molecular chaperones like HSP47 and ERp29, folding chaperones like Protein disulfide isomerase (PDI), Peptidyl prolyl cis-trans-isomerase (PPI) or ERp57, The stabilizers may also be or contain mono-, oligo and polysaccharides, preferably hydroxyethylstarch (HES), glycogen, amylase, dextran, dextrin, or inuline, xylose, mannose, glucose, fructose, galactose, ribose, fucose, glycerinaldehyd, dihydroxyaceton, lactose, lactulose, trehalose, maltose, sucrose, raffinose, mannitol, sorbitol, inositol, with or without amino-, N-acetyl-, hydroxyethy-, sulphate-modifications. The stabilizers can also comprise chaperons or caseins. Chaperons are proteins that assist the non-covalent folding/unfolding and the assembly/disassembly of other macromolecular structures, but do not occur in these structures when the latter are performing their normal biological functions.

Furthermore, the stabilizers may also be or contain ionic liquids or compatible solutes. An ionic liquid is a salt in which the ions are poorly coordinated, which results in these solvents being liquid. Ionic liquids are suggested to be suitable to protect substances coated thereby from potentially harmful material influences or radiation. In the context of the present invention, ionic liquids are believed to protect the biomolecules from decomposition upon sterilization. Compatible solutes are amphoteric, water-binding organic molecules that are characterized by their property to be excluded from protein surfaces.

The stabilizer may be or contain a saponin. Saponins are a class of chemical compounds forming secondary metabolites which are found in natural sources, derive from natural sources or can be chemically synthesized. Saponins are found in particular abundance in various plant species. Saponins are amphipathic glycosides grouped phenomenologically by the soap-like foaming they produce when shaken in aqueous solutions, and structurally by their composition of one or more hydrophilic glycoside moieties combined with a lipophilic triterpene derivative. Examples of saponins are glycyrrhicic acid, glycyrrhetinic acid, glucuronic acid, escin, hederacoside and digitonin. It is preferred that the saponin used as a stabilizer, when used in connection with medical applications according to the invention (see below) do not exert any pharmacological properties.

Preferably, the saponin is glycyrrhicic acid (also: glycyrrhizic acid) or a derivative thereof and the compatible solutes are ectoin or hydroxyectoin.

Derivatives of glycyrrhizic acid are well-known in the art and include those produced by transformation of glycyrrhizic acid on carboxyl and hydroxyl groups, by conjugation of amino acid residues into the carbohydrate part or the introduction of 2-acetamido-β-D-glucopyranosylamine into the glycoside chain of glycyrrhizic acid. Other derivatives are amides of glycyrrhizic acid, conjugates of glycyrrhizic acid with two amino acid residues and a free 30-COOH function and conjugates of at least one residue of amino acid alkyl esters in the carbohydrate part of the glycyrrhizic acid molecule. Examples of specific derivatives can be found e. g. in Kondratenko et al. (Russian Journal of Bioorganic Chemistry, Vol 30(2), (2004), pp. 148-153).

In a preferred embodiment, the at least one stabilizer and/or the at least one biomolecule is comprised in a buffered solution. The buffer to be used depends, inter alia, on the biomolecule which is to be covered/embedded. Buffers generally suitable for the contact with biomolecules are e. g. phosphate, citrate, acetate, borate, carbonate, lactate, ammonium, glycine, barbiturate, HEPES, MOPS, MES, TRIS. Exemplary buffers suitable for antibodies are described further below.

In another preferred embodiment, the at least one stabilizer or the stabilizing composition comprises an amino acid mixture of at least two different amino acids. In a more preferred embodiment of the present invention, the at least one stabilizer or the stabilizing composition comprises between 2 and 18 different amino acids, more preferably 2 to 10, even more preferably 2 to 8 and most preferably 2 to 5 or 5 to 8 different amino acids. Alternatively, the at least one stabilizer or the stabilizing composition comprises at least 2, at least 3, at least 4, at least 5, at least 6, at least 7 or at least 8 different amino acids or more such as at least 9, at least 10, at least 11, at least 12, at least 13, at least 14, at least 15, at least 16, at least 17, at least 18, at least 19 or at least 20 different amino acids. The number of different amino acids comprised in the at least one stabilizer or the stabilizing composition preferably does not exceed 18.

The amino acids that form the stabilizer or that are contained in the stabilizing composition can be selected from naturally occurring amino acids as well as artificial amino acids or derivatives thereof. Naturally occurring amino acids are e. g. the 20 proteinogenic amino acids glycine, proline, arginine, alanine, asparagine, aspartic acid, glutamic acid (according to the invention, said terms also include the salts of aspartic acid and glutamic acid), glutamine, cysteine, phenylanine, lysine, leucine, isoleucine, histidine, methionine, serine, valine, tyrosine, threonine and tryptophan. Other naturally occurring amino acids are e. g. carnitine, ornithine, hydroxyproline, homocysteine, citrulline, hydroxylysine or beta-alanine.

Derivates of amino acids are e.g. n-acetyl-tryptophan, phosphonoserine, phosphonothreonine, phosphonotyrosine, melanin, argininosuccinic acid and salts thereof or DOPA. Artificial amino acids are amino acids that have a different side chain length and/or side chain structure and/or have the amino group at a site different from the alpha-C-atom.

If the at least one stabilizer or the stabilizing composition comprises cysteine, it is preferred that it contains less than 1%, preferably less than 0.5% by dry weight cysteine within the mixture of at least two amino acids. This also applies to compositions comprising at least 3, at least 4, at least 5, at least 6, at least 7, at least 8, at least 9 or at least 10 amino acids or even more such as at least 11, at least 12, at least 13, at least 14, at least 15, at least 16, at least 17, at least 18, at least 19 or at least 20 amino acids.

Due to the SH group comprised in cysteine, compositions comprising cysteine may be subjected to oxidation taking place e. g. at the SH groups and resulting in displeasing odors and/or possibly the composition changing color to shades of brown. In order to minimize these undesired effects, in particular when the composition is used in connection with medical devices, the amount of cysteine comprised in the composition should be reduced as described above. However, even if these effects are undesired, they do not affect the suitability of compositions of the invention comprising a higher percentage of cysteines or otherwise exerting brownish colors or a displeasing odor.

In a more preferred embodiment, the at least one stabilizer or the stabilizing composition comprises an amino acid mixture of at least two different amino acids as defined above and a saponin which is preferably glycyrrhicic acid. In this embodiment, the stabilizer or the stabilizing composition preferably does not comprise proteins or fragments of proteins which are not amino acids, dipeptides and/or tripeptides. Accordingly, in this preferred embodiment of the present invention, the composition does not contain proteins or fragments thereof consisting of more than three amino acids, nor hydrolysed proteins that are of human or animal origin. Such a composition has the advantage that there is no risk of contaminating the bio-molecules embedded therein. It is furthermore a cost effective alternative to known stabilizing compositions.

In another more preferred embodiment, a saponin is comprised in said at least one stabilizer or a stabilizing composition comprising any number of different amino acids comprised in the above list of minimum numbers of amino acids, such as in a composition comprising at least 3, at least 4, at least 5, at least 6, at least 7, at least 8, at least 9 or at least 10 different amino acids or even more, such as at least eleven, at least 12, at least 13, at least 14, at least 15, at least 16, at least 17, at least 18, at least 19 or at least 20 different amino acids.

Especially preferred is composition comprising at least one amino acid of each group of (a) an amino acid with non polar, aliphatic R groups; and (b) an amino acid with polar, uncharged R groups; and (c) an amino acid with positively charged R groups; and (d) an amino acid with negatively charged R groups; and (e) an amino acid with aromatic R groups.

The naturally occurring amino acids can be classified into the above characteristic groups (Nelson D. L. & Cox M. M., 'Lehninger Biochemie' (2005), pp. 122-127) from each of which at least one amino acid is selected for the composition according to the invention. Also other than naturally occurring amino acids such as artificial amino acids can be classified accordingly. Whereas more than one amino acid of each group such as at least two or at least three can be comprised in the composition according to the invention, it is presently preferred that only one amino acid is selected from each group. The skilled person further understands that not the same number of amino acids of each group has to be present in the composition used according to the invention.

Rather, any combination of amino acids can be chosen as long as at least one amino acids of each group is present.

Especially preferred is a stabilizing composition wherein the amino acids comprised in the composition are alanine, glutamic acid, lysine, threonine and tryptophan. Another especially preferred stabilizing composition comprises aspartate, arginine, phenylalanine, serine and valine.

Also particularly preferred is at least one stabilizer or a stabilizing composition, wherein the amino acids comprised in the composition are or are selected from arginine, glycine, histidine, alanine, glutamic acid, lysine and tryptophan. This composition has been shown to be especially advantageous with regard to its properties after sterilization, in particular after irradiation. Said combination of amino acids was shown not to exert any displeasing odor or discoloration after irradiation. However, even if these effects are undesired, they do not affect the suitability of compositions of the invention comprising a higher percentage of cysteines or otherwise exerting brownish colors or a displeasing odor.

The biomolecules are reversibly attached to the carrier. The term "attached", as interchangeably used with the term "immobilized" or "immobilizing", relates to the fixation of biomolecules on the carrier.

The term "reversibly attached" defines that the biomolecules, when attached to the carrier, can be released from said carrier with suitable means. Depending on the kind of attachment, e. g. of whether the attachment is covalent or non-covalent, different means of releasing the biomolecules are applicable. Examples are cleavage by proteases, a pH change or a change in temperature. The biomolecules are attached to the carrier until needed and only then released from the carrier.

The techniques mentioned above are only examples for reversibly attaching biomolecules on solid carriers. It is emphasized that the present invention is not limited to these examples. Instead, any conventional method known in the state of the art can be applied which is suited for the reversible attachment of biomolecule(s) on a carrier.

The reversible attachment of the biomolecule is chosen in such a way that the biomolecule can be quickly released from the carrier. In this regard, the term "quickly" means that more than 50%, such as 60%, 70% or 80% of said biomolecule can be released within 2 hours or less, such as 1 hour, 30 minutes or 20 minutes, in any combination such as 60% in 30 minutes or 20 minutes, 70% in 30 minutes or 20 minutes or 80% in 30 minutes or 20 minutes, preferably more than 85% within 10 minutes or less and most preferably more than 98% within 1 minute. This can be achieved e. g. by applying one of the methods described below. Such a quick release makes the container of the invention suitable for medical or clinical applications (see below). Furthermore, the reversible attachment of the biomolecules is preferably chosen in such a way that the biomolecules are released immediately before the clinical application.

The reversible attachment can be covalent or non-covalent.

Preferably, the non-covalent bonds are non-covalent bonds with high affinity and specificity. Examples for such non-covalent bonds are those formed by the streptavidin-biotin or the avidin-biotin system. In this example, streptavidin/avidin is coupled covalently to a suitable carrier. The biotinylated biomolecule then is bound non-covalently but with high affinity to the streptavidin/avidin. By adding excess biotin, the binding is competitively suppressed and the biotinylated biomolecule is released.

The biomolecule may be attached via a linker, preferably a cleavable linker. Suitable linkers can be selected, but are not limited to
 a) linkers with disulfide-bridges like SDAD (NHS-SS-Diazirine), SulfoSAND, DSP that can easily be cleaved by the addition of reagents with -SH groups like thiols, mercaptanes, cystein, mecaptoethanol or dithiothreitol.
 b) linkers with peptide bonds which can be cleaved with a specific protease, preferably a human enzyme
 c) linkers which are cleavable via ultrasound
 d) linkers with ester bonds like EGS that can be cleaved by e.g. hydroxylamine
 e) linkers with Sulfons like BSOCOES that can be cleaved at higher ph (e.g. pH 11.6)
 d) linkers with cis-Diols like DST that can be cleaved by sodium-meta-periodate.

Alternatively, the biomolecules may be reversibly attached by drying as described in detail further below in connection with the methods of the invention. In this embodiment, reversible attachment is achieved in that the biomolecules and the molecule(s) used as a stabilizer and the solid carrier stick together after drying. Where the carrier is a stabilizer, the biomolecules and the molecules used as stabilizers stick together. Release of the biomolecules takes place upon addition of a liquid to the above compounds thus dissolving/solubilising the biomolecules and the stabilizing molecules.

The carrier can be two-dimensional or three-dimensional. The carrier may be planar, spherical, bead-like, a mesh, a net or a fibre-net In one preferred embodiment, the carrier is comprised in or forms part of the container. Useful containers for this embodiment are glass or plastic vials. The container surface may exhibit specific structures for this purpose in order to increase the surface, e.g. needle-like microstructures.

In another preferred embodiment and when the carrier is not a stabilizer, the carrier is a solid, preferably porous (e. g. a foam or sponge) container. Suitable carrier materials are selected from the group consisting of glass, medical grade stainless steel, metal alloys (e.g. chrome cobalt molybdenum, titan nitride oxide), hydroxyapatite, silicone, polystyrene, poly-L-lactic acid; polyurethane, polyester, polysulfone, polyethylene, polypropylene, polyacryl, polyacrylnitril, polyamid, PMMA, fleece wadding, open porous foam, plastic or glass and reticular plastic or glass and structures derived from marine sponges (porifera) or (sintered) ceramics.

Other preferred solid carriers are a mesh, a fibre net or sintered material.

In a further preferred embodiment, the carriers are beads. The beads can be separated from the biomolecules by filtration or, if magnetic beads like Dynabeads® or MACS®-beads are used, by magnets. In addition, nano-beads may be used which can be injected as biomolecule-bead complex into the patient.

In a further preferred embodiment, the carrier is semi-solid. The material of the semi-solid carrier can be selected, for example, from gels that are capable of swelling like hydrogels (e.g. PolyHema) or gelatinous protein mixtures (e.g. Matrigel). In a different preferred embodiment, the carrier is solubilizable. Solubilizable carriers may be selected from soluble polymers, e.g. polysaccharides, polypeptides or polyethyleneglycols. Further solubilizable carriers include crystals or ionic liquids. Generally, the carriers which are stabilizers according to this invention are solubilizable.

In a more preferred embodiment the solubilizable carrier comprises, preferably proteinaceous, structures and/or carbohydrate structures that dissolve in aqueous, optionally buffered solutions.

In a preferred embodiment, the container is inwardly essentially free of aerial oxygen. In this embodiment, the term "essentially free" refers to a very low content of aerial oxygen within the container of the invention as compared to that of air. Accordingly, "essentially free of aerial oxygen" denotes a content of aerial oxygen within the container of less than 10%, preferably less than 5%, more preferably less than 2%, even more preferably less than 1% and most preferably between 0 and 1%.

In another preferred embodiment, the container is inwardly essentially free of liquid, preferably water. In this embodiment, the term "essentially free" refers to a very low content of liquid, preferably water within the container of the invention as compared to the total volume of biomolecule and stabilizer or the water free content of the container. Accordingly, "essentially free of liquid" denotes a content of liquid within the container of less than 10%, preferably less than 5%, more preferably less than 2% such as less than 1%, 0.5% or 0.2%.

The above two embodiments result in a further enhancement in the stability of the biomolecules attached to the stabilizer/carrier and subjected to sterilization by optimizing the environmental conditions within the container. For example by removing liquid from the container, sterilization is even less prone to destroy biomolecules attached to the carrier/stabilizer within the container since fewer reactive oxygen species may evolve from applying radiation to liquids such as water.

In an alternative preferred embodiment, the container is producible or produced by the method of the present invention as described below.

In another embodiment, the present invention relates to a method for producing a container for biomolecules, comprising: (a) inserting a carrier into a container; (b) reversibly attaching at least one biomolecule to said carrier; (c) incubating the carrier with the at least one reversibly attached biomolecule in a solution comprising at least one stabilizer selected from (poly)peptides such as dipeptides or tripeptides, amino acids, carbohydrates, polyalcohols, polyethylenglycols, ionic liquids, compatible solutes, saponins or a mixture thereof, such that the at least one biomolecule is partially or completely covered by said at least one stabilizer; (d) sealing the container; and (e) sterilizing the container.

For the case that the carrier is a stabilizer, the invention relates to a method for producing a sterilized container for biomolecules, comprising: (a) inserting at least one carrier which is a stabilizer selected from (poly)peptides such as dipeptides or tripeptides, amino acids, polyalcohols, polyethylenglycols, ionic liquids, compatible solutes, saponins or a mixture thereof into a container; (b) reversibly attaching at least one biomolecule to said carrier such that the at least one biomolecule is partially or completely covered by said at least one carrier; (c) sealing the container; and (d) sterilizing the container.

The invention furthermore relates to a method for producing a container for biomolecules, comprising: (a) reversibly attaching at least one biomolecule to a carrier, (b) inserting the carrier with the at least one attached biomolecule into a container, (c) incubating said carrier with the at least one reversibly attached biomolecule in a solution comprising at least one stabilizer selected from (poly)peptides such as dipeptides or tripeptides, amino acids, carbohydrates, polyalcohols, polyethylenglycols, ionic liquids, compatible solutes, saponins or a mixture thereof, such that the at least one biomolecule is partially or completely covered by said at least one stabilizers, (d) sealing the container; and (e) sterilizing the container.

In yet another embodiment, the present invention relates to a method for producing a container for biomolecules, comprising: (a) reversibly attaching at least one biomolecule to a carrier, (b) incubating the carrier with the at least one reversibly attached biomolecule in a solution comprising at least one stabilizer selected from (poly)peptides such as dipeptides or tripeptides, amino acids, carbohydrates, polyalcohols, polyethylenglycols, ionic liquids, compatible solutes, saponins or a mixture thereof, such that the at least one biomolecule is partially or completely covered by said at least one stabilizer, (c) inserting the carrier with the at least one reversibly attached biomolecule into a container, (d) sealing the container; and (e) sterilizing the container.

For the case that the carrier is a stabilizer, the invention relates to a method for producing a sterilized container for biomolecules, comprising: (a) reversibly attaching at least one biomolecule to a carrier which is a stabilizer selected from (poly)peptides such as dipeptides or tripeptides, amino acids, polyalcohols, polyethylenglycols, ionic liquids, compatible solutes, saponins or a mixture thereof, such that the at least one biomolecule is partially or completely covered by said at least one stabilizers, (b) inserting the carrier with the at least one attached biomolecule into a container, (c) sealing the container; and (d) sterilizing the container.

In a further embodiment, the present invention provides a method for producing a terminally sterile container for biomolecules, comprising following steps:
(a) reversibly attaching the biomolecules to a carrier,
(b) inserting the carrier with the attached biomolecules into the container,
(c) incubating the carrier in a composition comprising one or more stabilizers selected from
(poly)peptides, amino acids, starch, sugars, phosphates, polyalcohols, polyethyleneglycols or a mixture thereof, such that the biomolecules are partially or completely covered by said one or more stabilizers,
(d) closing the container,
(e) terminally sterilizing the container.

Steps (a), (b) and (c) can be performed in different sequences: (a), (b) and (c) can be performed consecutively. Alternatively, step (b) can be performed before step (a) and then be followed by step (c). In a third alternative, the sequence is first (b), then (c), then (a).

The definitions given for the container of the invention and the preferred embodiments described above in connection with said container, where applicable, mutatis mutandis apply to the above methods of the present invention, in particular as regards the nature and/or composition of the carrier and/or stabilizer or stabilizing composition, the biomolecules and the methods relating to attachment or release of the stabilizer and/or the carrier and/or the biomolecules. This includes in particular the preferred embodiments relating to the stabilizer being an amino acid mixture and preferred additional constituents such as a saponin, and the particularly preferred embodiments thereof.

In another alternative applicable to the methods of the invention, the reversible attaching of the biomolecule to the carrier and/or the incubation in the solution comprising at least one stabilizer is done in bulk production comprising a cutting step prior to the insertion of the coated carrier into the container. Methods of bulk production are well-known to the skilled person.

The insertion of the carrier with the attached biomolecules can be performed manually or automated.

The closing of the container can, for example, be performed by applying a lid (e.g. a rubber stopper) or by melting the opening in case of glass or plastic containers which are formed only by one piece.

A major advantage of the method and thereby produced carrier of the present invention is that the biomolecule comprising container can be (terminally or bulk) sterilized. The term 'terminal sterilization' in the context of the present invention means that the sterilization can be performed at the end of the production process, namely after the biomolecules and the stabilizer have been attached to the carrier and said carrier has been inserted into the container. Suitable sterilization methods comprise, but are not limited to ethyleneoxide (EO) treatment, (dry) heat or acid pH treatment, solvent-detergent (SD) treatment, X-rays, autoclaving or plasma sterilization. Especially preferred is irradiation, mostly preferred beta or gamma irradiation.

Thus, the (terminal or bulk) sterilization allows the production of the biomolecule-comprising container under non-sterile or semi-sterile conditions. Due to this feature, the production costs can be greatly reduced compared to the costs for the production of conventional containers for biomolecules that have to be produced under completely sterile, i.e. aseptic conditions.

However, the sterilization does not have to be necessarily at the end but rather can be done at another time after the addition of the at least one stabilizer. Another advantage of the sterilization method of the present invention is that no freezing is required for the sterilization of the biological materials. This is very advantageous as therefore the biofunctionality of the biological material that is to be sterilized can be greatly enhanced compared to methods known in the state of the art, e.g. U.S. Pat. No. 5,730,933.

In a further preferred embodiment, the at least one stabilizer comprises or is a saponin, preferably glycyrrhizic acid or a derivative thereof. Suitable derivatives have been defined above.

In another preferred embodiment, the method of the present invention further comprises a step of drying the biomolecules. This step is preferably performed after incubating the carrier with the at least one reversibly attached biomolecule or, where the carrier is a stabilizer, reversibly attaching at least one biomolecule to said carrier in a solution comprising at least one stabilizer as described above. Where reversible attachment is achieved in that the biomolecules and the molecules used as a stabilizer (e. g. amino acids, optionally in connection with a saponin and/or optionally in connection with at least one di- and/or tripeptide as described) stick together after drying, the step of reversible attaching comprises drying the carrier together with the biomolecule. Release of the biomolecules corresponding to the reversibility of the attachment takes place upon addition of a liquid to the above compounds sticking together thus dissolving/solubilising the biomolecules and the stabilizing molecules from the carrier. Preferably, the biomolecules are dried until the residual liquid content is less than 10%, preferably less than 5%, more preferably less than 2% such as less than 1%, 0.5% or 0.2% of the originally applied composition. Preferred drying methods include, but are not limited to methods which are used for removing the stabilizing composition such as air-drying, spray-drying, lyophilisation and precipitation. Further suitable techniques comprise crystallization and microcrystallization.

The method according to the present invention may further comprise step (f), i.e. the elution of the biomolecules from the carrier. The elution method applied depends on the carrier used and may comprise, but is not limited to solutions with high salt concentrations, biotin-containing solutions, or solutions containing proteases or SH-containing substances.

In a further embodiment, the present invention comprises a container where a solution is applied which detaches the biomolecule from the carrier, preferably with a rate of more than 50%, such as 60%, 70% or 80% of the attached biomolecules within 2 hours or less, such as 1 hour, 30 minutes or 20 minutes, in any combination such as 60% in 30 minutes or 20 minutes, 70% in 30 minutes or 20 minutes or 80% in 30 minutes or 20 minutes, more preferably more than 85% within 10 minutes and most preferably more than 98% within 1 minute. The detachment of the biomolecule(s) from the carrier can e. g. be effected by cleavage of the non-covalent and or covalent bonds due to high or low ion strength, changes in pH, and or sulfhydryl-group containing substances, hydroxylamines, periodates, proteases, which are present in said solution.

In another embodiment, the biomolecule(s) are detached from the carrier by the help of ultrasound and or irradiation, preferably by infrared, visible or ultraviolet light.

A further advantage of the method according to the present invention is that the biomolecule-comprising containers produced by said method are suited for long-time storage. The introduction of new or modified products to the medical marketplace requires the assurance that they can be stored for an extended period (from one to five years) without any major decrease in performance that may affect safety and efficacy when the products are used. Because full-period, ambient-aged samples usually do not exist for such products, it is generally necessary to conduct 'accelerated-aging' tests to provide experimental data in support of performance and shelf-life claims for these products until full-period samples become available.

A simplified approach for accelerated aging is based on testing at a single accelerated temperature and then employing the rule stating that the rate of a chemical reaction will increase by factor $Q_{10}$ for every 10° C. increase in temperature. The typical relationship selected for commonly used medical polymers is $Q_{10}$=2; that is, a doubling of the reaction rate for each 10° C. increase in the temperature above use or storage temperature.

In order to achieve a sufficient shelf life for biomolecules that are used for diagnosis or therapy, these biomolecules usually have to be frozen in order to prevent their denaturation (Cleland et al., (2001), Journal or Pharmaceutical Sciences Vol. 90, pp. 310-321). Furthermore, the biomolecules of interest have to be incubated in stabilizing solutions containing so-called lyoprotectants such as sugars (e.g. sucrose, trehalose, mannnitol) or salts. However, due to the risk that biomolecules are denatured by freezing, a need exists for storage methods at 4° C. or at room temperature, especially for unstable biomolecules like e.g. IgM antibodies.

Surprisingly, it was found that by providing biomolecules in a container according to the present invention (i.e. reversibly attached on/in a carrier, totally or partially (i. e. preferably at least 20%, preferably at least 30%, more preferably at least 40%, at least 50%, at least 60, at least 70%, even more preferably at least 80%, at least 90%, at least 95% such as at least 98 or 99%) covered by at least one stabilizer according to the present invention, said biomolecules can be stored up to 7 days at 45° C. without significant loss of their biological activity. According to the rule described earlier, this 'accelerated aging' equals to a storage of 16 weeks at 5° C.

Preferred storage temperatures are from −273° C. to −15° C., especially preferred are temperatures from 2° C. to 8° C. and from 2° C. to 30° C.

In a preferred embodiment of the container or the methods of the invention, the at least one stabilizer and/or the at least one biomolecule is comprised in a buffered, preferably aqueous solution. The buffer to be used depends, inter alia, on the biomolecule which is to be covered/embedded. Buffers generally suitable for the contact with biomolecules are e. g. phosphate, citrate, acetate, borate, carbonate, lactate, ammonium, glycine, barbiturate, HEPES, MOPS, MES, TRIS.

In another preferred embodiment of the container or the methods of the invention, said stabilizer comprises less than 1%, more preferably less than 0.3% Tween, preferably Tween 80.

Tween is a generic term for polysorbates which are a class of emulsifiers and surfactants used in some pharmaceuticals and food preparations. They are often used to solubilize oily ingredients into water-based products. Polysorbates are oily liquids derived from PEG-ylated sorbitan (a derivative of sorbitol) esterified with fatty acids. Examples for polysorbates are polysorbate 20 (Tween 20 or polyoxyethylene (20) sorbitan monolaurate), polysorbate 40 (Tween 40 or polyoxyethylene (20) sorbitan monopalmitate), polysorbate 60 (Tween 60 or polyoxyethylene (20) sorbitan monostearate), and polysorbate 80 (Tween 80 or polyoxyethylene (20) sorbitan monooleate). Tween 80 is most preferred in the compositions used in the present invention.

In the course of the present invention, it has been found that the addition of less than 1% Tween (preferably related to the dry mass of biomolecules and amino acids) avoids foaming during handling of the liquid composition according to the invention.

In a preferred embodiment, the method of the invention, prior to sealing the container and after reversibly attaching the at least one biomolecule or inserting the carrier with the at least one attached biomolecule into a container, removing aerial oxygen from the container and/or removing liquid, preferably water from the container.

As described above in connection with the container of the invention, the features of the above embodiment further enhance the stability of the biomolecules attached to the stabilizer/carrier and subjected to sterilization by optimizing the environmental conditions within the container. For example by removing liquid from the container, sterilization is even less prone to destroy biomolecules attached to the carrier/stabilizer within the container.

In a different embodiment, the present invention relates to a method for the production of a sterile solution comprising at least one biomolecule comprising: (a) conducting the method for producing a container for biomolecules according to the invention; and (b) eluting the at least one biomolecule from the carrier; and optionally (c) simultaneously with, prior to or after step (b), applying a renaturing solution which enables structurally denatured biomolecules to renature.

Alternatively, the steps (b) and (c) of this embodiment may form part of the methods for producing a sterilized container of the invention described further above.

The term "eluting" relates to the release of the at least one reversibly attached biomolecules from the carrier. Elution may be effected using a, preferably buffered, aqueous solution, such as a buffered or not buffered salt solution, or water under suitable conditions depending on the kind of attachment, i. e. whether it is covalent or non-covalent as described above.

Elution rates have already been described above. A suitable elution rate as defined above makes the container of the invention suitable for medical applications where a device needs to be prepared for medical applications within a few minutes. In this embodiment, elution may be effected by injecting a suitable, preferably aqueous solution into the container and the applying it to the patient so that the eluted biomolecules can leave the container and spread within the patient's body.

Preferably, the renaturing solution comprises chaperons (e.g. heat shock proteins of the Hsp100/Clp-family, the Hsp90-family, the Hsp70-family, the Hsp60/GroEL-family and the small heat shock proteins (sHsps). General chaperones are e. g. BiP, GRP94, GRP170, lectin chaperones are e. g. calnexin and calreticulin, non-classical molecular chaperones are e.g. HSP47 and ERp29, folding chaperones are e. g. protein disulfide isomerase (PDI), peptidyl prolyl cis-trans-isomerase (PPI), ERp57, ionic liquids and or arginine.

In a preferred embodiment, after step (b) and optionally (c), the method for the production of a sterile solution further comprises applying the eluted at least one biomolecule onto a column or a filter. Suitable columns or filters are e.g. ion exchange columns such as DEAE, cholestyramin, polyethylenimine coupled to a suitable matrix like sepharose or styrol, or size exclusion columns such as Sepharose G25 or columns filled with charcoal.

Said applying corresponds to the purification of the biomolecule containing solution directly after release of the biomolecule from its carrier and/or during the infusion into a patient. This step enables the removal of substances, that might be damaging for the attached biomolecules as well as the removal of denatured biomolecules, which might have been formed during the sterilization process.

The container according to the present invention can be used for diagnostic, prophylactic and therapeutic applications. Accordingly, the container of the invention may form part of a medical or diagnostic device. Such devices being a combination of the biological component comprising the biomolecules stabilized according to the invention and a non biological part are also termed biological-device combination product.

Therapeutic devices include medical implants, catheters, stents, tubings, alone or in combination with other components or medical devices used in extracorporeal circulation.

The therapy approaches may comprise in vivo as well as ex vivo applications of the container of the invention in the context of a medical device. Accordingly, a device comprising the container of the invention can be implanted into a patient for an in vivo application to gradually release the biomolecule upon applying a (body)liquid into the container. For an ex vivo application a device comprising the container of the invention can be connected with the circulation of a body liquid to be treated. Blood derived from an artery or a vein of a patient may be e.g. led through such device and subsequently piped back into the patient (connection with the blood stream). Alternatively, samples of a body fluid may be incubated with the carrier in vitro. In a subsequent step of the latter treatment the body fluid can be reintroduced into the body of a patient. All these applications necessitate the application of a liquid into the container to dissolve the biomolecules comprised therein which then may act e. g. as a drug.

The term "patient" as used throughout the present invention comprises ill or diseased as well as healthy subjects. A patient in accordance with the present invention is any person who receives medical attention, care, or treatment. The person is most often but not always ill or injured and, if so, in need of treatment by a physician or other medical professional. In other terms, the term "patient" is interchangeably used with "subject" which may or may not be ill. The subject can be an animal, preferably a mammal, most preferably a human. In accordance with the above, a patient is also, for example, a healthy human who is, on an acute or routine basis, diagnosed for a disease or health status.

The figures show:

FIG. 1

A vial is shown comprising a carrier with the reversibly attached biomolecule and the protective coating. The biomolecule (e.g. cytokine) is embedded by the stabilizer solution and thereby protected against stress influences like dehydration during storage or irradiation during sterilization.

FIG. 2

Different carriers are shown:
a) The carrier is a non dissolvable gel or a dissolvable gel
b) The carrier is a non woven fibre network
c) The carrier is a mesh or woven network
d) The protective coating itself is the carrier and covers the biomolecule or the vial itself is the carrier
e) The carrier has an open porous (like a sponge) or sintered structure
f) The carrier comprises of nano-, micro- or macro-particle
g) The vial itself is the carrier and has micro or macro structures that increase the surface (e.g. needle like structures).

FIG. 3

An example is shown, where the vial itself is the carrier. First, the biomolecule was attached to the carrier by drying. Subsequently, the stabilizer solution was added and also dried. The biomolecule (here interleukin 8=IL8) loses most of its biological function during subsequent sterilisation (25 kGy irradiation) if no stabilizer is added. In contrast both stabilizer solution A (Albumin and Mannitol) and B (solution with different amino acids) protected the biomolecule. Shown is the chemotactic activity of IL8 on human neutrophil granulocytes.

FIG. 4

An example is shown, where the vial itself is the carrier. First, the biomolecule was attached to the carrier by drying. Subsequently, the stabilizer solution was added and also dried. The biomolecule (here interleukin 8=IL8) loses most of its biological function during accelerated storage (45° C.) if no stabilizer is added. In contrast both stabilizer solution A (Albumin and Mannitol) and B (solution with different amino acids) protected the biomolecule. Shown is the chemotactic activity of IL8 on human neutrophil granulocytes.

FIG. 5

An example is shown, where the vial itself is the carrier. First, the biomolecule was attached to the carrier by drying. Subsequently, the stabilizer solution was added and also dried. The biomolecule (here ds-DNA) loses part of its biological function during subsequent sterilisation (25 kGy irradiation) if no stabilizer is added. In contrast both stabilizer solution A (Albumin and Mannitol) and B (solution with different amino acids) protected the biomolecule. Shown is the detectable DNA amount in percent of staring value.

FIG. 6

An example is shown, where the stabilizer itself is the carrier. The biomolecule and the stabilizer solution were added and dried together. The biomolecule (here interleukin 8=IL8) loses most of its biological function during subsequent sterilisation (25 kGy irradiation) if no stabilizer is added. In contrast both stabilizer solution A (Albumin and Mannitol) and B (solution with different amino acids) protected the biomolecule. Shown is the chemotactic activity of IL8 on human neutrophil granulocytes.

FIG. 7

An example is shown, where the stabilizer itself is the carrier. The biomolecule and the stabilizer solution were added and dried together. The biomolecule (here an anti-mouse IgG antibody) loses most of its biological function during subsequent storage and or sterilisation (25 kGy irradiation) if no stabilizer is added. In contrast both stabilizer solution A (Albumin and Mannitol) and B (solution with different amino acids) protected the biomolecule. Shown is the specific binding to the antigen.

FIG. 8

Influence of different desorption solutions on the biological activity of a biomolecule (here an anti-mouse IgG antibody). With the exception of 0.5 M $H_2SO_4$ none of the other desorption solution tested in this experiment had a significant influence on the biological activity of the biomolecule. Shown is the specific binding to the antigen.

FIG. 9

The desorption of a biomolecule (here an anti-mouse IgG antibody) is tested after the biomolecule was attached to an open porous polyurethane foam (supplier A, large pores). While citrate buffer pH 4.75 and 1 M NaCl only desorbed small amounts of the biomolecule, significantly more biomolecule could be desorbed with 1 M NaCl+0.02 M imidazole and phosphate buffered saline, respectively. Shown is the specific binding to the antigen.

FIG. 10

The desorption of a biomolecule (here an anti-mouse IgG antibody) is tested after the biomolecule was attached to an open porous polyurethane foam (supplier B, smaller pores). Citrate buffer pH 4.75 and phosphate buffered saline desorbed a little bit better than 1 M NaCl with or without 0.02 M imidazole. Shown is the specific binding to the antigen.

FIG. 11

The desorption of a biomolecule (here an anti-mouse IgG antibody) is tested after the biomolecule was attached to an open porous polyurethane foam (supplier Smith&Nephews, small pores). The biomolecule (here an anti-mouse IgG antibody) loses most of its biological function during subsequent storage and or sterilisation (25 kGy irradiation) if no stabilizer is added. In contrast a stabilizer solution (Albumin and Mannitol) protected the biomolecule. The recovery of the antibody is almost 100% (5 µg/ml). Shown is the specific binding to the antigen.

FIG. 12

The desorption of a biomolecule (here an anti-mouse IgG antibody) is tested after the biomolecule was attached to a PVA-hydrogel. The biomolecule loses most of its biological function during subsequent storage and or sterilisation (25 kGy irradiation) if no stabilizer is added. In contrast a stabilizer solution A (Albumin and Mannitol) and B (solution with different amino acids) protected the biomolecule. The recovery of the eluted antibody is very high. Shown is the specific binding to the antigen.

FIG. 13

Chemical Structures of examples for cleavable linkers

FIG. 14

Anti-Hepatitis A test (functional ELISA) of an amino acid composition used for protecting anti Hepatitis antibodies after lyophilisation and sterilization.

FIG. 15

The structural class of saponins has the potential to enhance the protective effect of amino acid combinations. Preferred is the use of the saponin glycyrrhizic acid.

FIG. 16

Combinations of at least 3 amino acids and combinations of 2 amino acids with the addition of glycyrrhizic acid provide a maximal protection of an immobilized antibody when sterilized with 50 kGy beta irradiation.

FIG. 17

The amino acid composition provides protection under different stress conditions. The best protection is provided for beta irradiation with different doses and artificial aging under elevated temperature. The protection for gamma irradiation or ethylene oxide sterilisation is less but still relevant.

Figure 18:
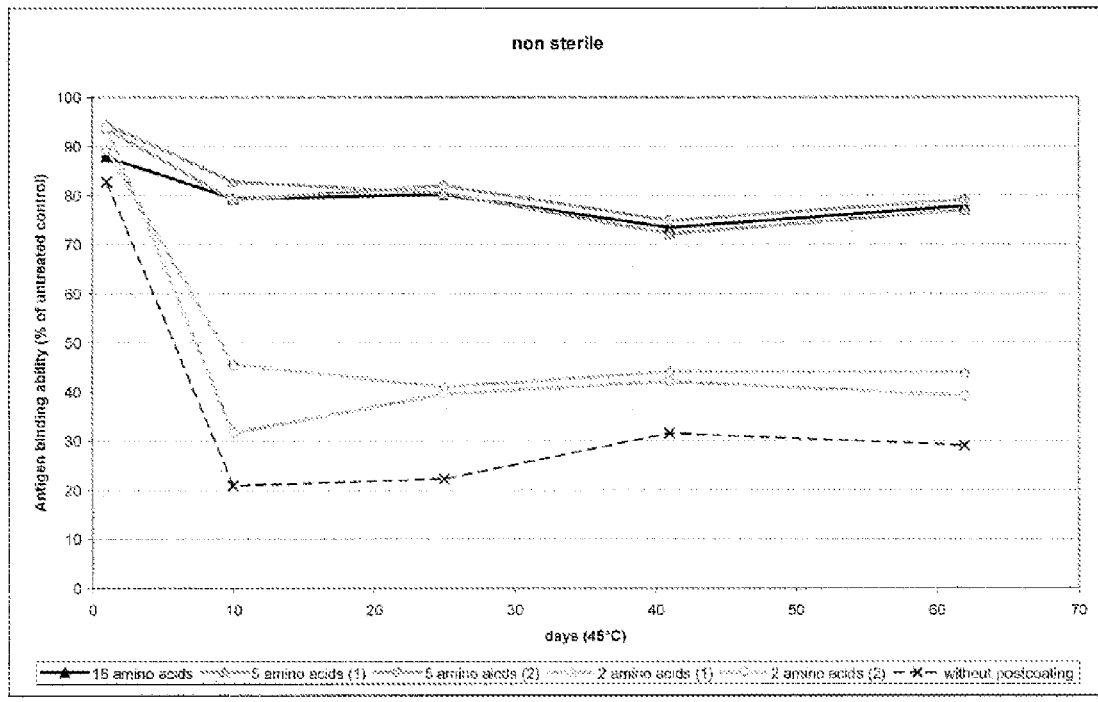
Figure 19:
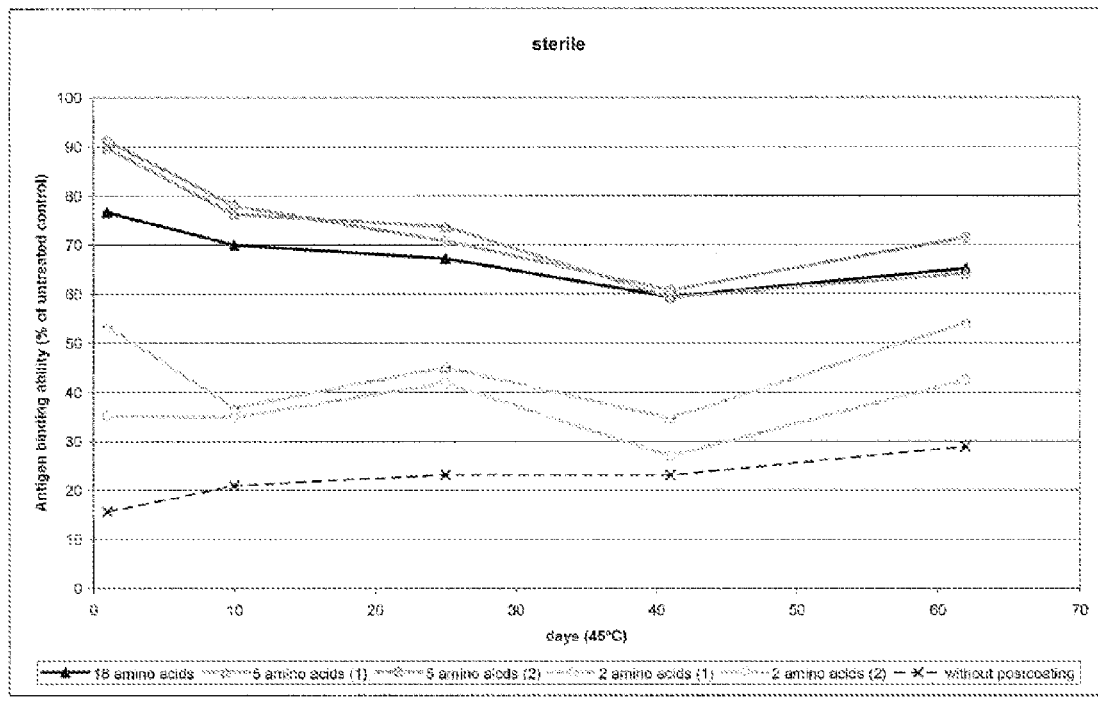

FIGS. 18 and 19

Amino acid postcoatings containing at least 5 amino acids provide protection during longtime storage. For the non sterilized samples, after 62 days at 45° C. about 80% of the antigen binding ability is preserved. Sterilized samples (beta, 25 kGy) maintain about 70% of their antigen binding ability after 62 days at 45° C. Amino acid postcoatings containing only 2 amino acids maintain only about 40% antigen binding ability during the storage process, regardless of sterilization. Without postcoating only 20-30% activity is preserved.

Figure 20:
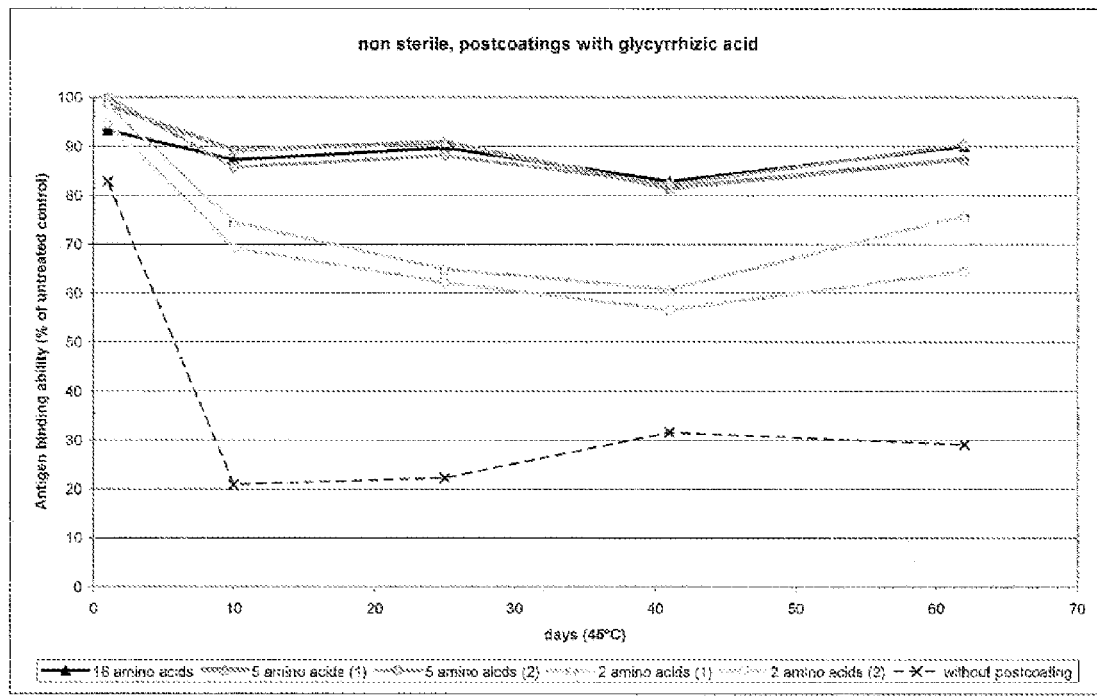
Figure 21:
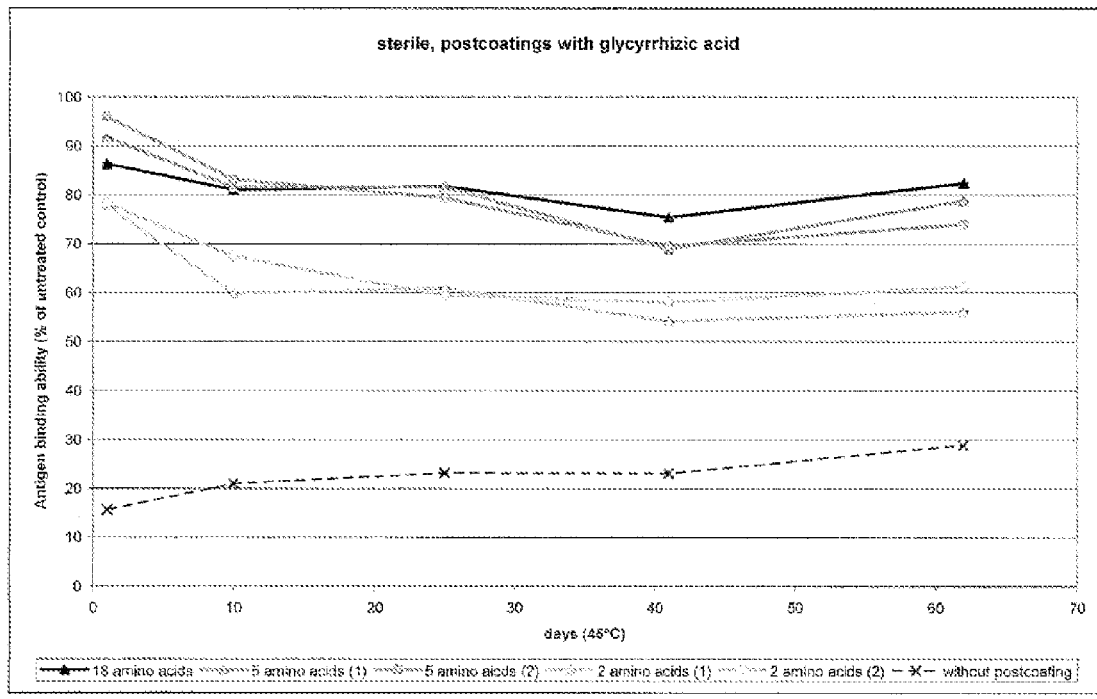
Figure 22:
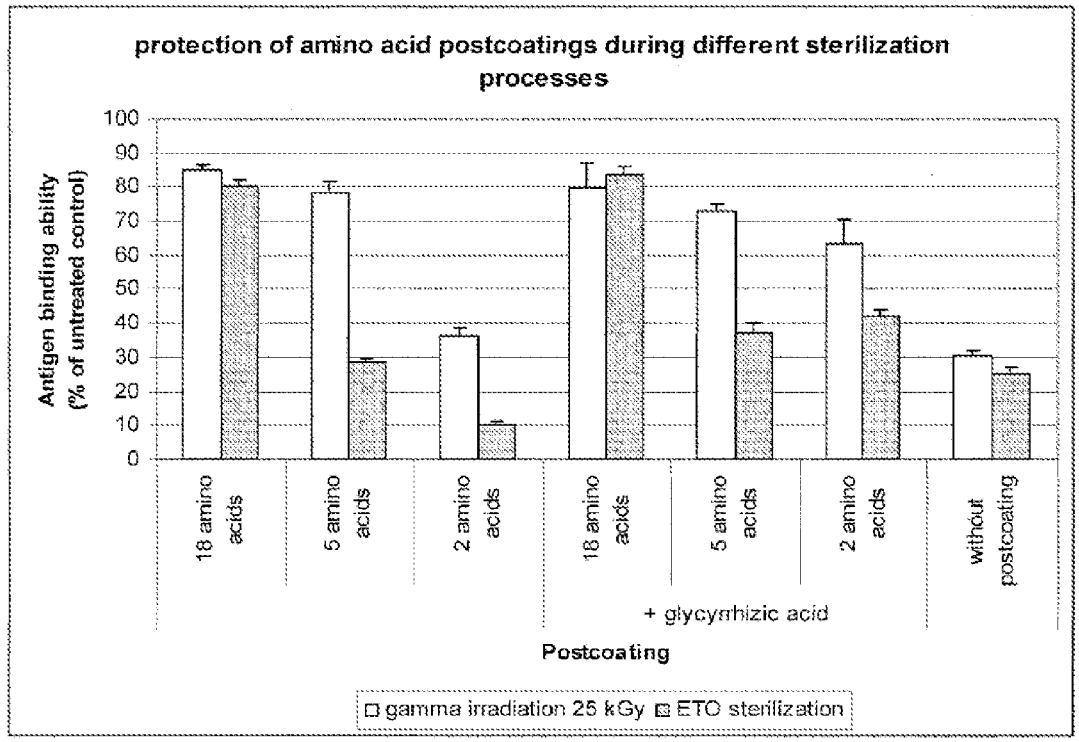
Figure 23:
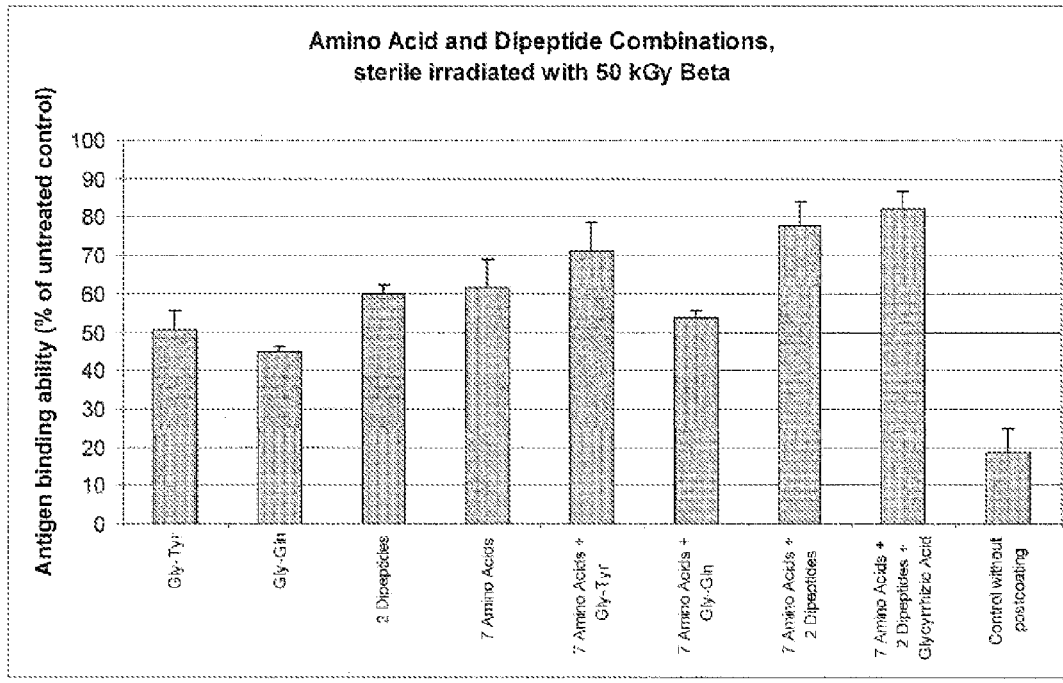

FIGS. 20 and 21

The addition of 1 mM glycyrrhizic acid to the postcoating solutions enforces the protecting effect. Amino acid postcoatings containing at least 5 amino acids and glycyrrhizic acid provide protection during longtime storage. For the non sterilized samples, after 62 days at 45° C. about 90% of the antigen binding ability is preserved. Sterilized samples (beta, 25 kGy) maintain about 80% of their antigen binding ability after 62 days at 45° C. Amino acid postcoatings containing 2 amino acids and glycyrrhizic acid maintain about 70% antigen binding ability during the storage process, regardless of sterilization. Without postcoating only 20-30% activity is preserved.

FIG. 22

Samples sterilized with gamma irradiation maintain about 85% activity when protected with an amino acid postcoating containing 18 amino acids; this effect is not further enhanced with glycyrrhizic acid; with 5 amino acids the remaining activity is 75%; with 2 amino acids only 40% are maintained. The protection with 2 amino acids is improved by the addition of glyccyrhizic acid, here the remaining activity is 65%. Samples sterilized with ETO maintain about 85% activity when protected with an amino acid postcoating containing 18 amino acids; this effect is not further enhanced with glycyrrhizic acid. Postcoatings containing 5 or 2 amino acids have only little protecting effect; the addition of glycyrrhizic acid enhances the protection marginally.

FIG. 23

Amino acid postcoating of amino acids, dipeptides or mixtures thereof, optionally together with glycyrrhizic acid.

The examples illustrate the invention.

EXAMPLE 1

Interleukin-8 in Glass-Vials was Sterilized, the Vial Itself is the Carrier

Experiment:

Interleukin-8 (IL-8, R&D, 208-IL) was diluted in PBS (without $Ca^{2+}/Mg^{2+}$, PAA, H15-002) to 10 µg/ml. 5 µl of the solution (50 ng IL-8) were added to glass vials and rotated for 4 hours until dried. 25 µl of a stabilizing solution (A=20 g/l albumin (Biotest Pharma) and 10 g/l mannitol (Serag Wiesner, 219675), B=20 g/l amino acid mixture and 1 mM glyzyrrhizic acid (ammonium salt, Fluka, 50531)) were added and rotated/dried over night.

The vials were sterilized with ≥25 kGy (beta irradiation). Unsterilized controls were stored under cool conditions.

Assay:

Neutrophil granulocytes were isolated from 10% ACDA whole blood. 20 ml ACDA blood (10%) were sedimented with 2 ml HES (Grifols 662650). The supernatant was pipetted to 7 ml Percoll (L6143) and centrifuged 20 min at 2000×g. The isolated granulocytes were resuspended in 1% autologous serum and set to a cell count of $0.5×10^6$/ml.

As positive controls 5 µl IL-8-solution (50 ng) were dissolved in 25 µl of the stabilizing solution (A and B). To each sterile vial 1 ml PBS (with $Ca^{2+}/Mg^{2+}$, Hyclone, SH3026401) (with 1% autologous serum) were added to dissolve the dried film.

To detect the chemotactic activity of the samples, the complete IL-8 solutions from the sterile and non-sterile vials and the controls were pipetted into 12-well-plates. Migration filters (3 µm, Corning, 3462) were inserted and 500 µl of the granulocyte suspension was pipetted into the filters. The plates were incubated for 30 min at 37° C. The number of migrated cells was detected by counting the cells in each well via FACS and counting beads (Invitrogen, C36950).

Figure 3:
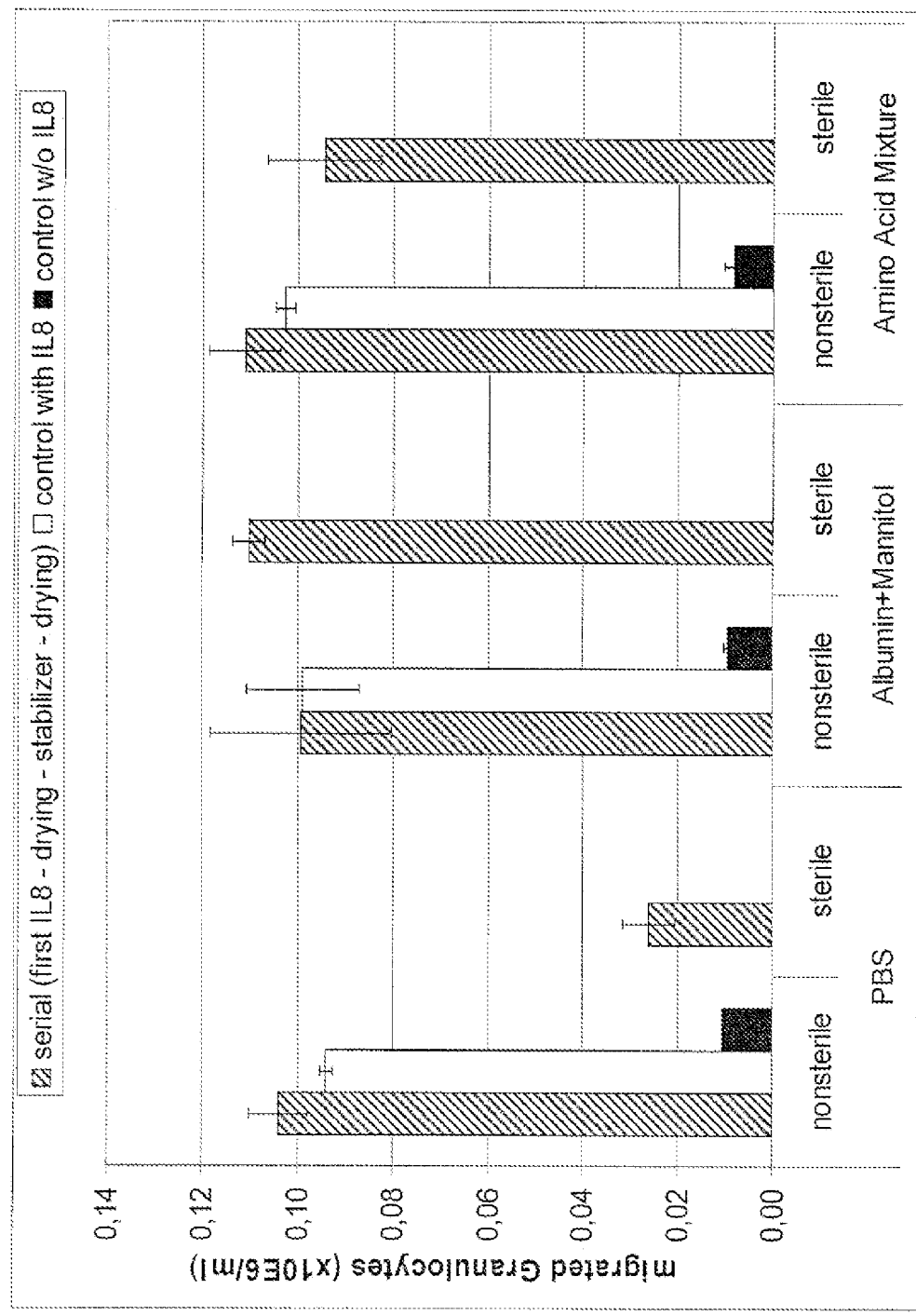
Figure 4:
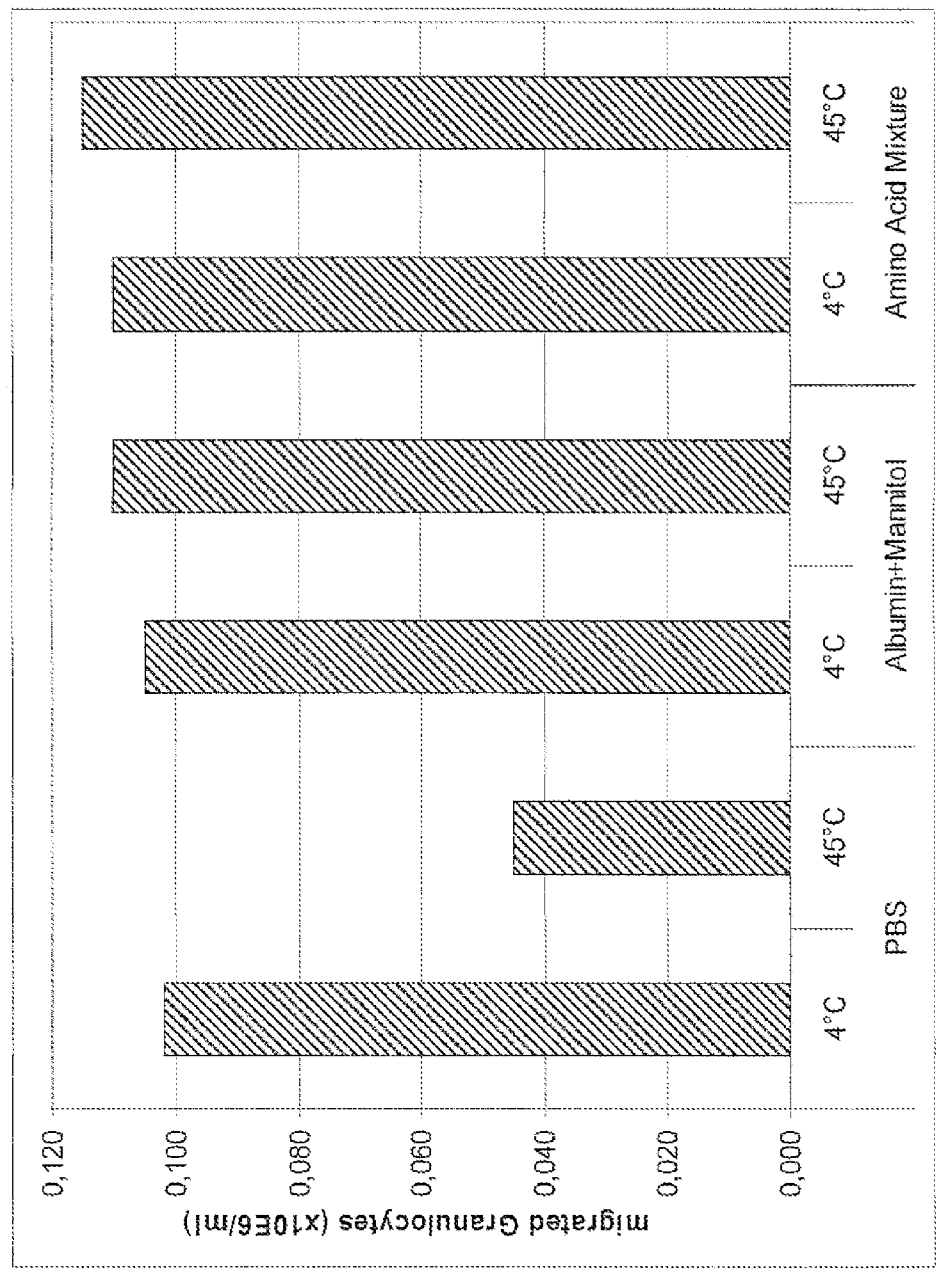
Figure 5:
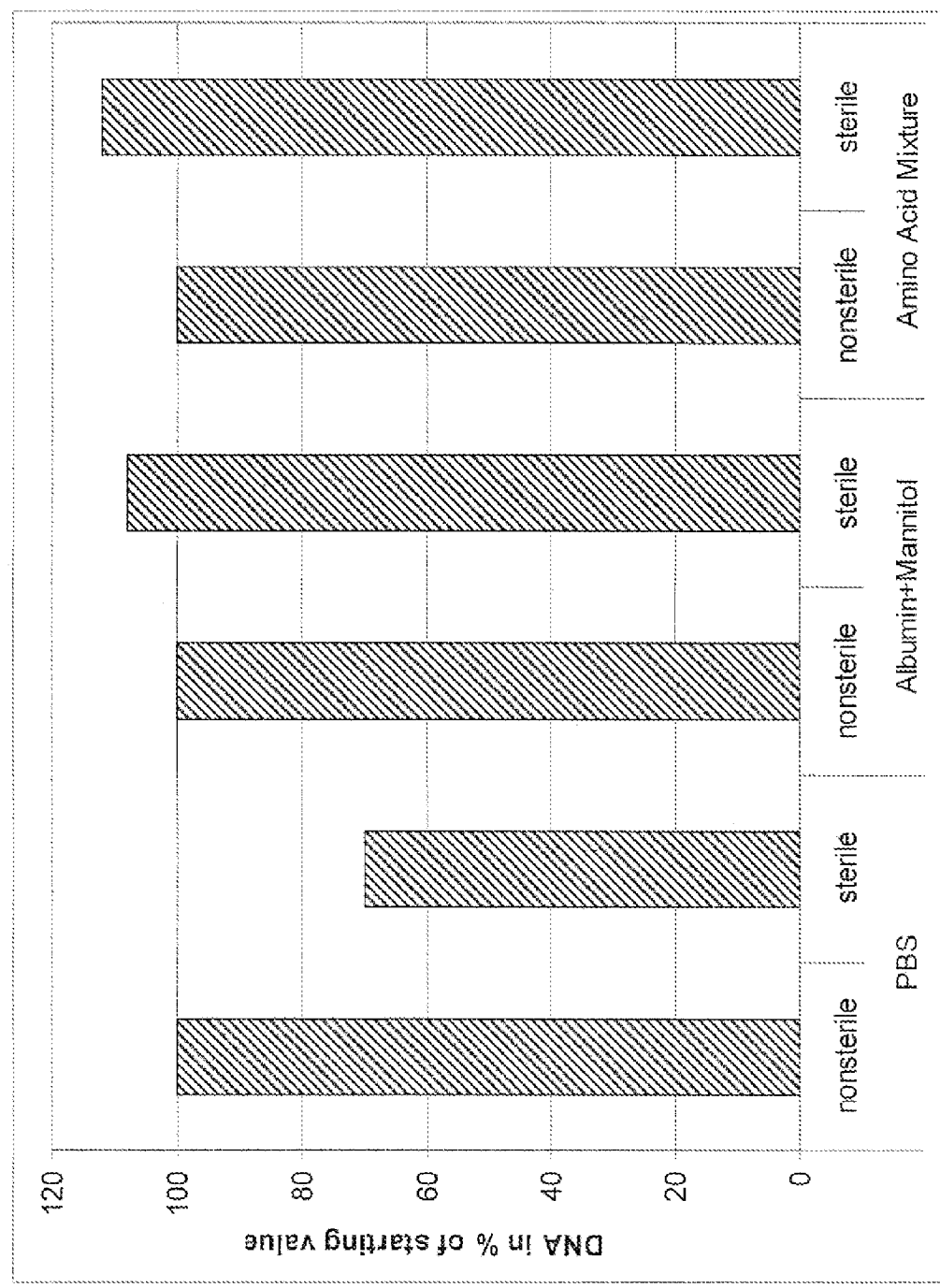

Results:

See FIG. 3

The biomolecule (here interleukin 8=IL8) loses most of its biological function during subsequent sterilisation (≥25 kGy irradiation) if no stabilizer is added. In contrast both stabilizer solution A (Albumin and Mannitol) and B (solution with different amino acids) protected the biomolecule. Shown is the chemotactic activity of IL8 on human neutrophil granulocytes.

EXAMPLE 2

Interleukin-8 in Glass-Vials was Sterilized, the Stabilizer Itself is the Carrier Experiment:

Interleukin-8 (IL-8) was diluted in PBS (without $Ca^{2+}/Mg^{2+}$, PAA, H15-002) to 10 µg/ml. 5 µl of the solution (50 ng IL-8) and 25 µl of an stabilizing solution (A=20 g/l albumin (Biotest Pharma) and 10 g/l mannitol (Serag Wiesner, 219675), B=20 g/l amino acid mixture and 1 mM glyzyrrhizic acid (ammonium salt, Fluka, 50531)) were mixed and pipetted into glass vials. The vials were rotated/dried over night.

The vials were sterilized by irradiation with ≥25 kGy. Unsterilized controls were stored under cool conditions.

Assay:

Neutrophil granulocytes were isolated from 10% ACDA whole blood. 20 ml ACDA blood (10%) were sedimented with 2 ml HES (Grifols 662650). The supernatant was pipetted to 7 ml Percoll (L6143) and centrifuged 20 min at 2000×g. The isolated granulocytes were resuspended in 1% autologous serum and set to a cell count of $0.5×10^6$/ml.

As positive controls 5 µl IL-8-solution (50 ng) were dissolved in 25 µl of a stabilizing solution (A and B). To each sterile vial 1 ml PBS (with $Ca^{2+}/Mg^{2+}$, Hyclone, SH3026401) (with 1% autologous serum) were added to dissolve the dried film.

To detect the chemotactic activity of the samples, the complete IL-8-solutions from the sterile and non-sterile vials and the controls were pipetted into 12-well-plates. Migration filters (3 µm) were inserted and 500 µl of the granulocyte suspension was pipetted into the filters. The plates were incubated 30 min at 37° C. The number of migrated cells was detected by counting the cells in each well (via FACS and counting beads).

Figure 6:
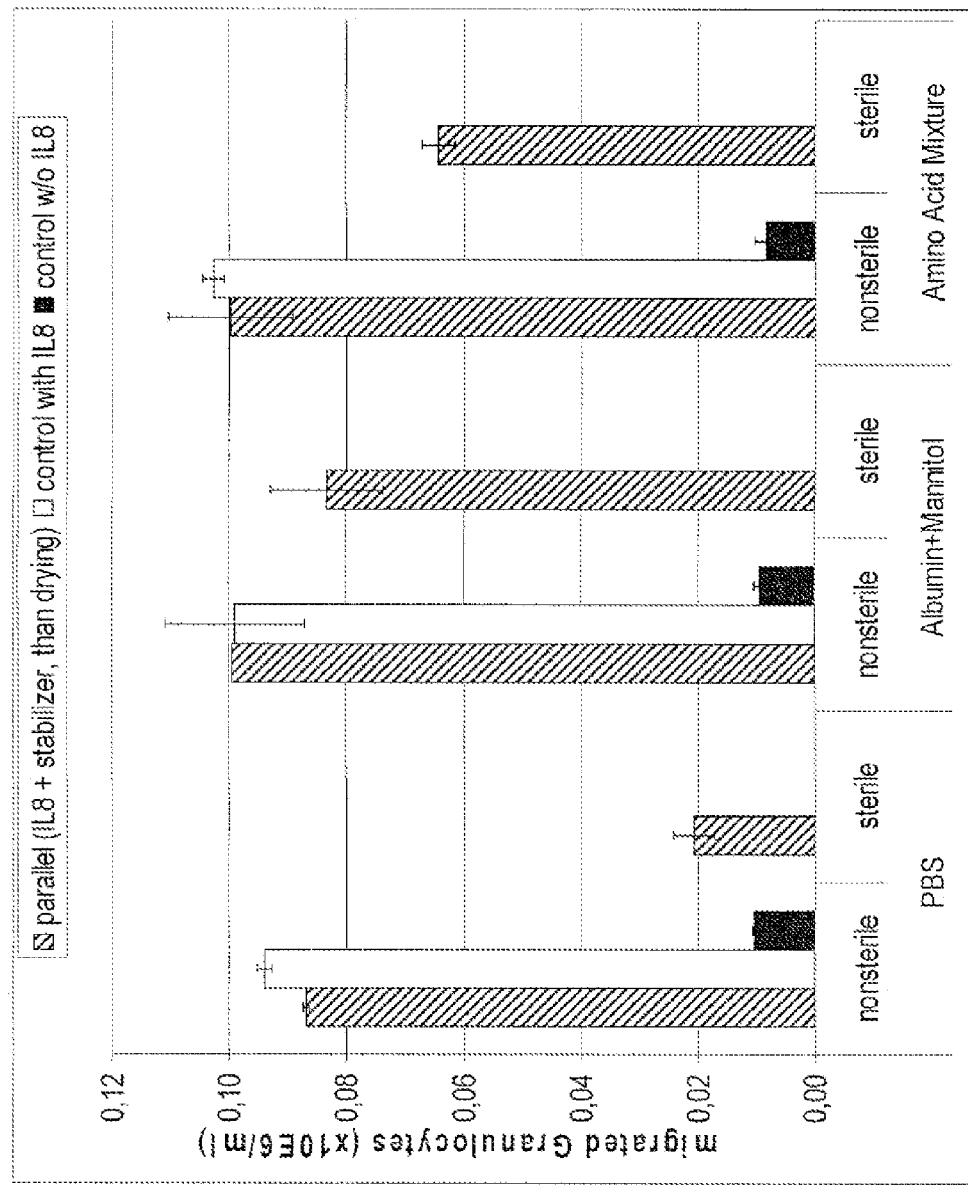

Results:

See FIG. 6

The biomolecule (here interleukin 8=IL8) loses most of its biological function during subsequent sterilisation (≥25 kGy irradiation) if no stabilizer is added. In contrast both stabilizer solution A (Albumin and Mannitol) and B (solution with different amino acids) protected the biomolecule. Shown is the chemotactic activity of IL8 on human neutrophil granulocytes.

EXAMPLE 3

Anti-Mouse-IgG in Glass-Vials was Sterilized, the Stabilizer Itself is the Carrier Experiment:

Anti-Mouse-IgG (biotinylated, Jackson ImmunoResearch, 115-065-003) was diluted in PBS (without $Ca^{2+}/Mg^{2+}$, PAA, H15-002) to 4 µg/ml. 25 µl (100 ng) of the antibody solution and 25 µl of an 2×concentrated stabilizing solution (A=20 g/l albumin (Biotest Pharma) and 10 g/l mannitol (Serag Wiesner, 219675), B=20 g/l amino acid mixture and 1 mM glyzyrrhizic acid (ammonium salt, Fluka, 50531)) were mixed and pipetted into glass vials. The vials were rotated/dried over night.

The vials were sterilized by irradiation with ≥25 kGy. Unsterilized controls were stored under cool conditions.

Assay:

An ELISA plate (Greiner Bio-one, 655061) was coated with the antigen (mouse IgG, Innovativ Research, Ir-Ms-Gf): the antigen was diluted to 1 µg/ml, 100 µl were pipetted to each well and incubated over night at 4° C. The plate was washed twice with washing buffer (25× concentrate, Invitrogen, WB02). The plate was blocked with Albumin (5%) and washed again 3 times.

To all sample vials 200 µl PBS were added to dissolve the dried film (theoretically 5 µg/ml). The samples were diluted to 10 ng/ml with PBS. To calculate the antibody concentration a serial dilution of fresh antibody was prepared.

The samples and standard were pipetted to the ELISA plate (2×200 µl each) an incubated 1 h at ambient temperature. The plate was washed 3×. To each well 200 µl Streptavidin solution (Horseradish peroxidase (HRP) labelled, Pierce, 21126, diluted to 0.1 µg/ml in PBS) were added and incubated 1 h at ambient temperature. The plate was washed 3×. HRP chromogenic substrate TMB (TMB=tetramethylbenzidine, Invitrogen, 00-2023) was diluted 1:2 in H2O and 200 µl were added to each well. The plate was incubated 15 min at ambient temperature and was protected from light. To stop the color reaction 50 µl diluted H2SO4 (diluted 1:5 with aqua dest., Merck, 1007311000) were added. The absorption of the plate was detected at 450 nm (Fusion Photometer A153601, PerkinElmer).

Figure 7:
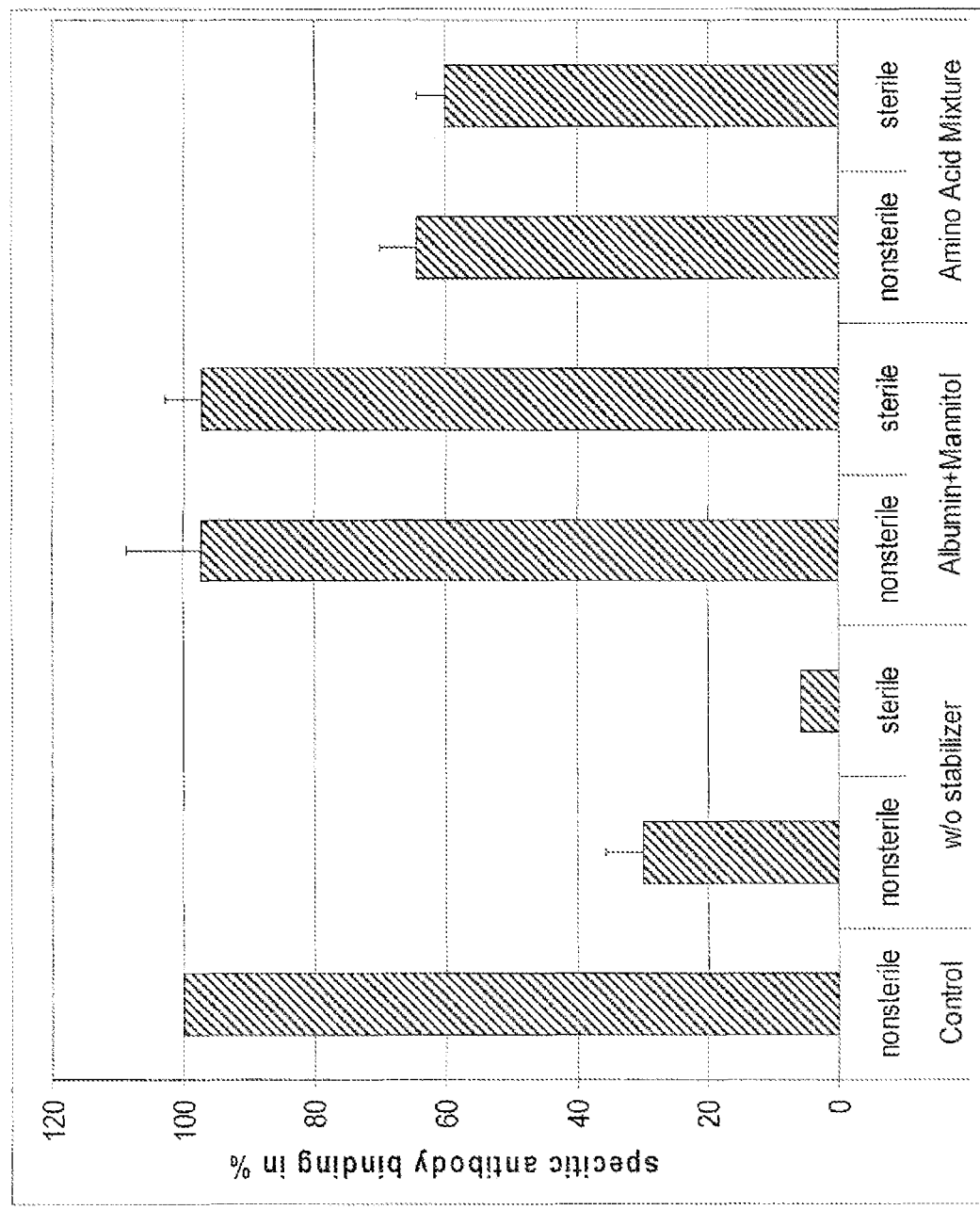
Figure 8:
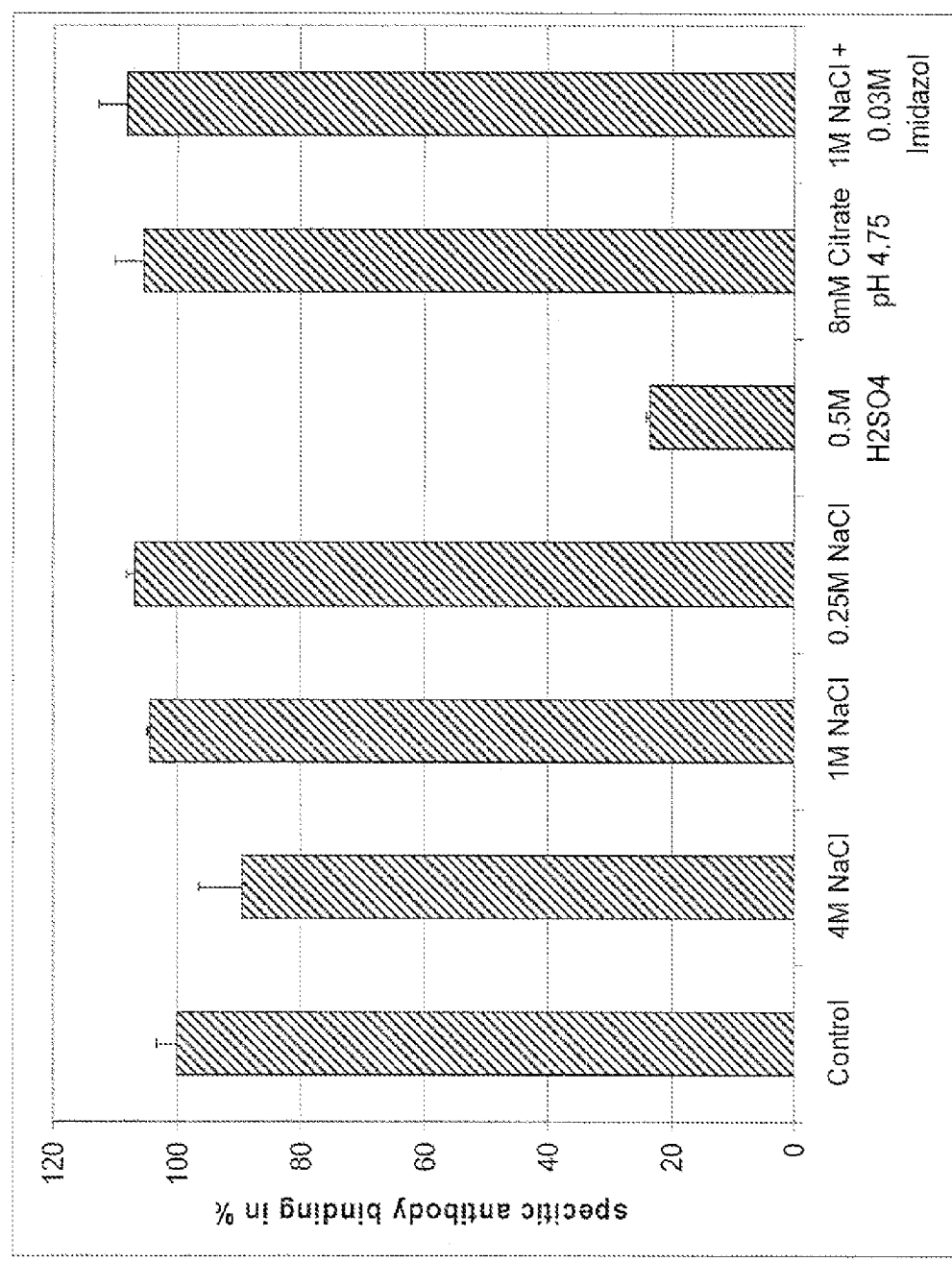
Figure 9:
Figure 10:
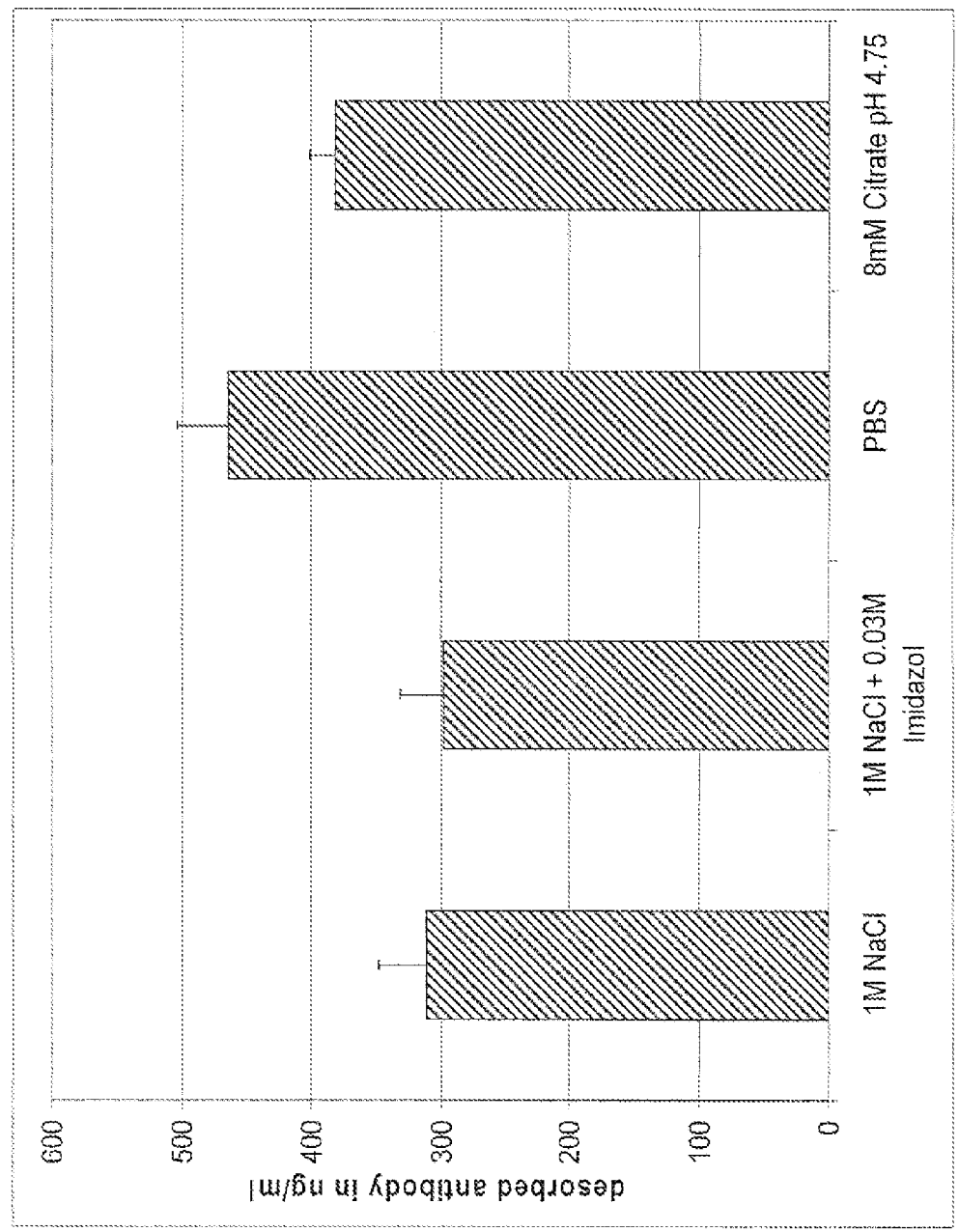
Figure 11:
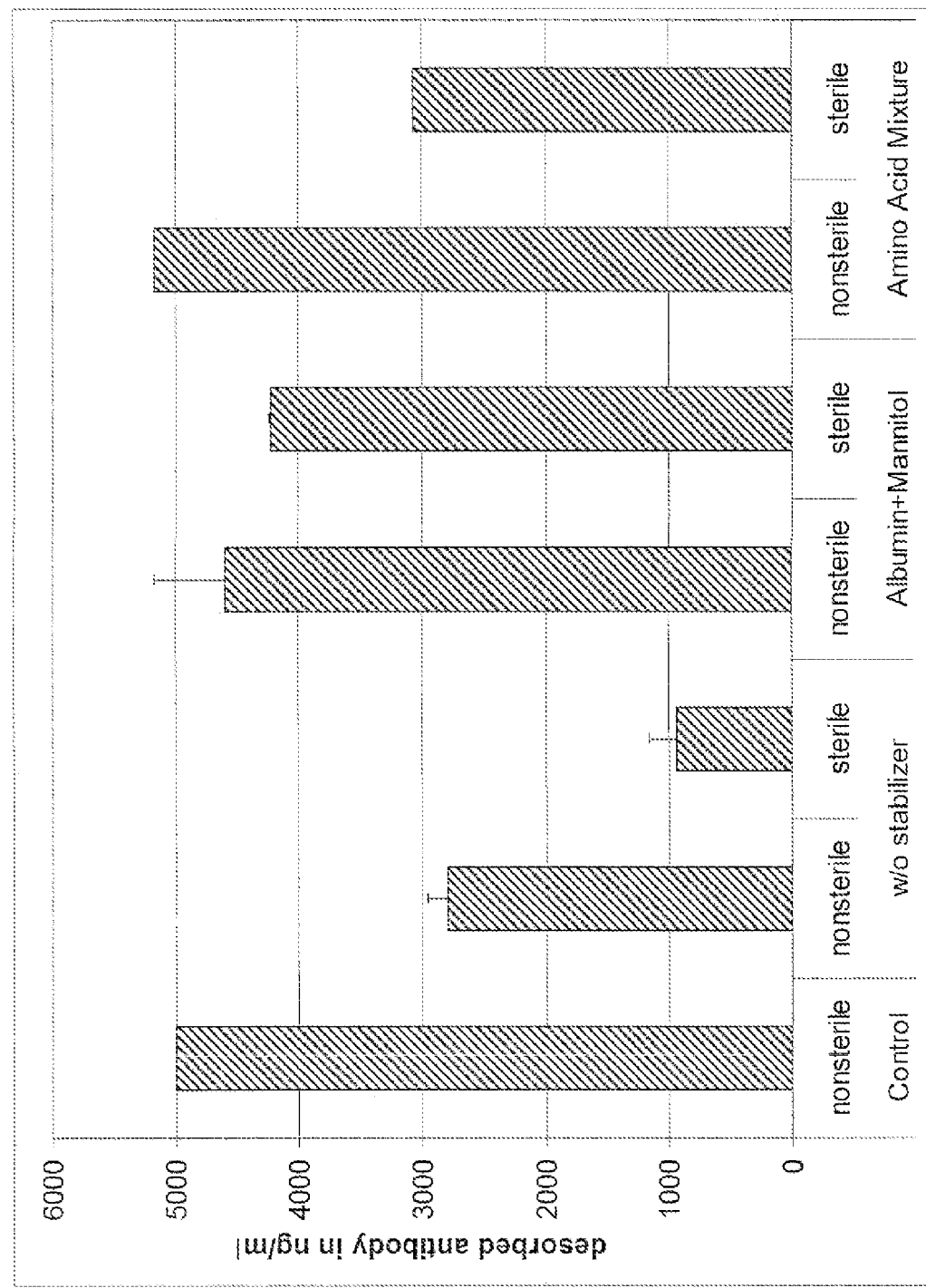
Figure 12:
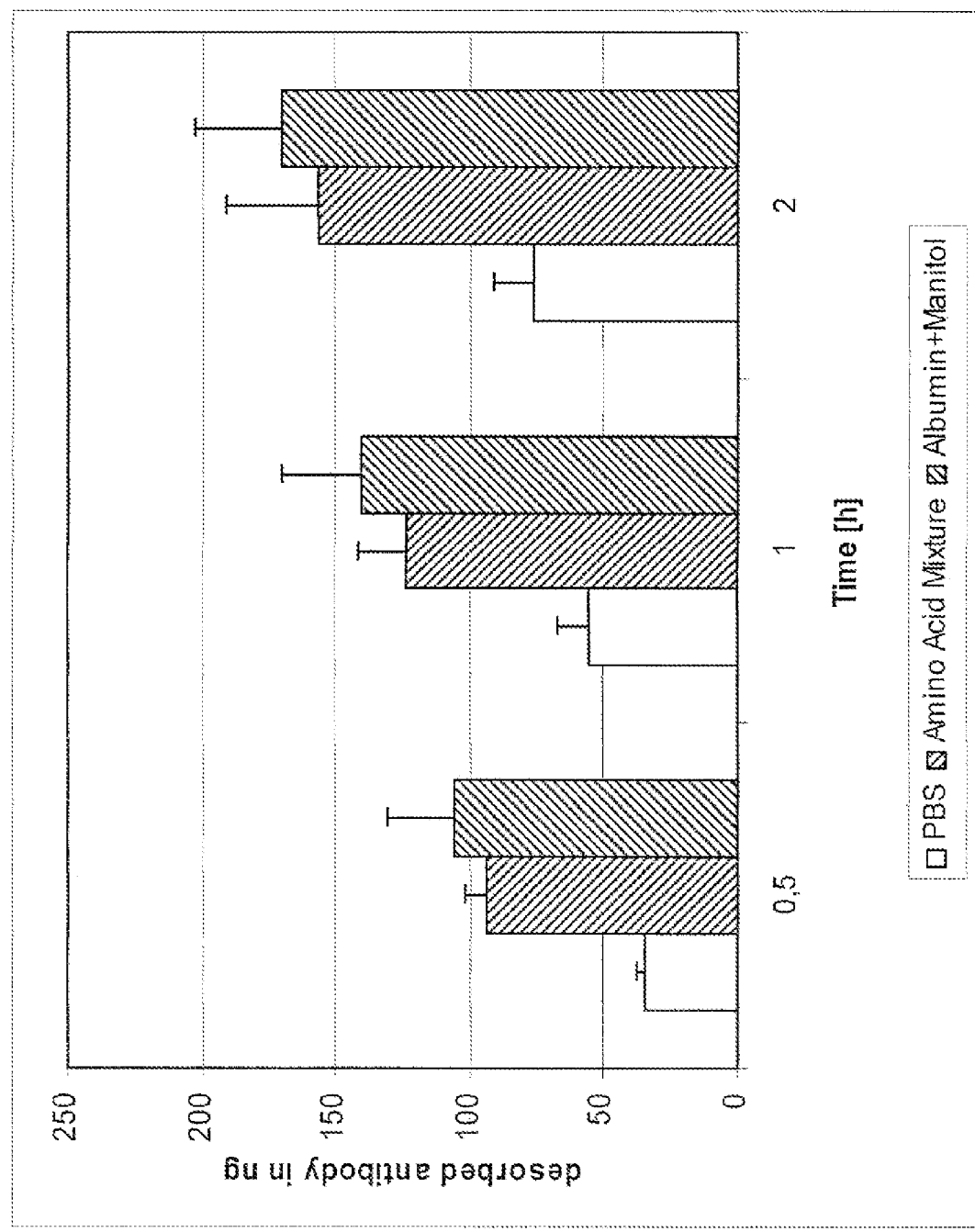
Figure 13:
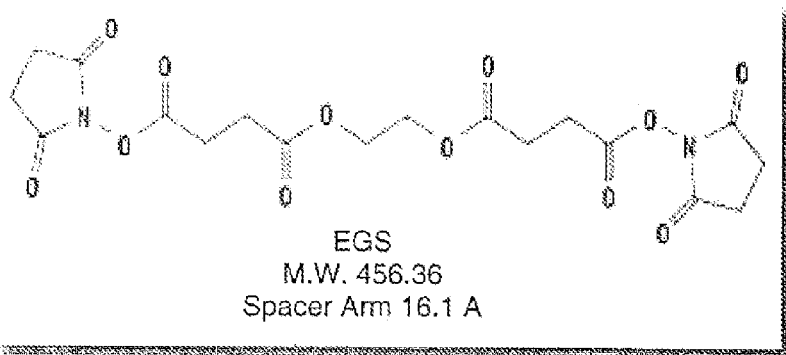
Figure 13:
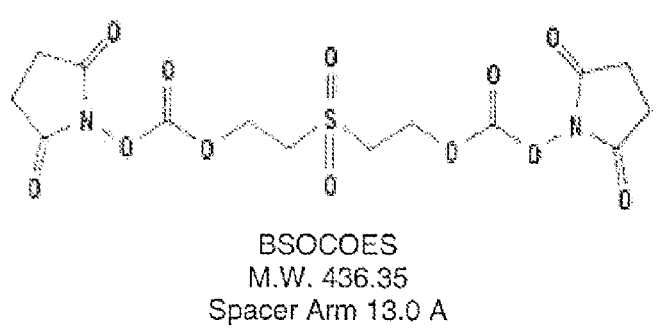
Figure 13:
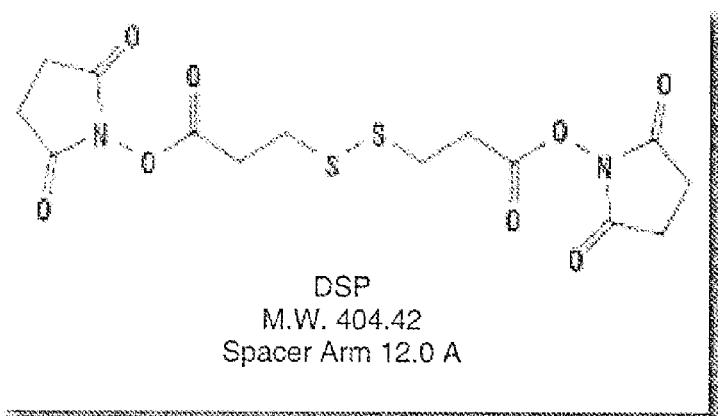
Figure 13:
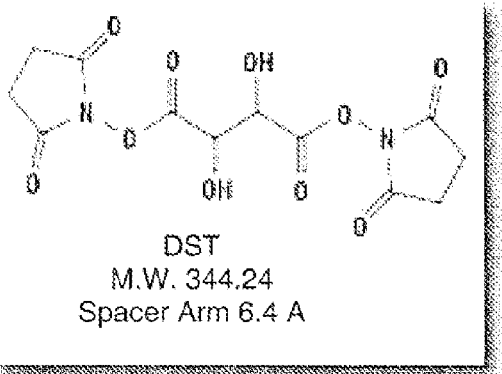
Figure 13:
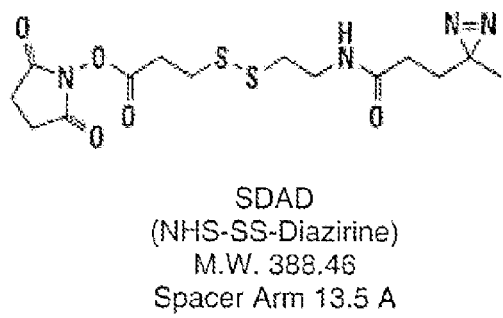
Figure 13:
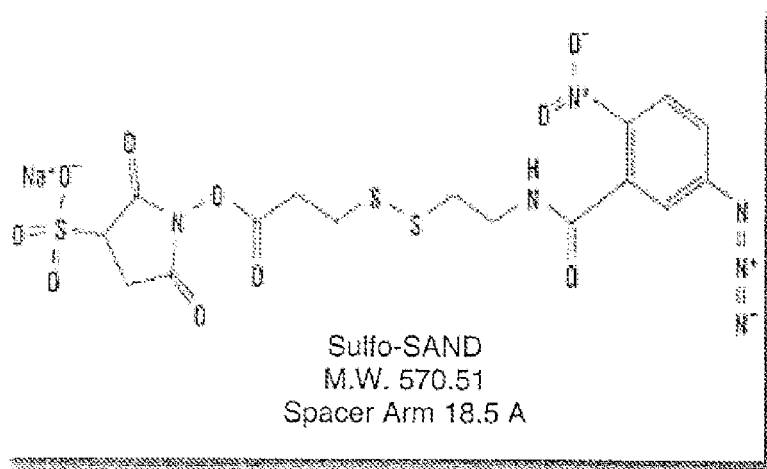

Results:

See FIG. 7

The biomolecule (here an anti-mouse IgG antibody) loses most of its biological function during subsequent storage and or sterilisation (≥25 kGy irradiation) if no stabilizer is added. In contrast both stabilizer solution A (Albumin and Mannitol) and B (solution with different amino acids) protected the biomolecule. Shown is the specific binding to the antigen.

EXAMPLE 4

Anti-Mouse-IgG was Sterilized, the Carrier is a Polyurethane Foam

Experiment:

From a fine porous polyurethane (PU) foam (Smith&Nephew, 66012608) samples with a defined diameter (1 cm) were punched. Anti-Mouse-IgG (biotinylated, Jackson ImmunoResearch, 115-065-003) was attached to the samples: the antibody was diluted to 5 µg/ml either in PBS (without $Ca^{2+}/Mg^{2+}$, PAA, H15-002) or in a stabilizing solution (20 g/l albumin (Biotest Pharma) and 10 g/l mannitol (Serag Wiesner, 219675) in PBS) and the PU samples were covered with antibody solutions. The samples were incubated for 1 h at 37° C.

The antibody solution was removed and the PU samples were air dried for 2 h. The samples were sterilized via beta irradiation (25 kGy) and unsterile controls were stored under cool conditions.

Assay:

An ELISA plate (Greiner Bio-one, 655061) was coated with the antigen (mouse IgG, Innovativ Research, Ir-Ms-Gf): the antigen was diluted to 1 µg/ml, 100 µl were pipetted to each well and incubated over night at 4° C. The plate was washed 2× with washing buffer (25× concentrate, Invitrogen, WB02). The plate was blocked with Albumin (5%) and washed again 3×.

The PU samples were covered with PBS and incubated 1 h at ambient temperature. The sample solutions were collected and diluted 1:20 and further serial diluted 1:4 with PBS. To calculate the antibody concentration of the samples a serial dilution of fresh antibody was prepared.

The samples and standard were pipetted to the ELISA plate (2×200 µl each) and incubated 1 h at ambient temperature. The plate was washed 3×. To each well 200 µl Streptavidin solution (Horseradish peroxidase (HRP) labeled, Pierce, 21126, diluted to 0.1 µg/ml in PBS) were added and incubated 1 h at ambient temperature. The plate was washed 3×. HRP chromogenic substrate TMB (TMB=tetramethylbenzidine, Invitrogen, 00-2023) was diluted 1:2 in $H_2O$ and 200 µl were added to each well. The plate was incubated 15 min at ambient temperature and was protected from light. To stop the color reaction 50 µl diluted H2SO4 (diluted 1:5 with aqua dest., Merck, 1007311000) were added. The absorption of the plate was detected at 450 nm (Fusion Photometer A153601, PerkinElmer).

Results:

The biomolecule (here an anti-mouse IgG antibody) loses most of its biological function during subsequent storage and or sterilisation (25 kGy irradiation) if no stabilizer is added. In contrast a stabilizer solution (Albumin and Mannitol) protected the biomolecule. The recovery of the antibody is almost 100% (5 µg/ml). Shown is the specific binding to the antigen.

EXAMPLE 5

Anti-Mouse-IgG was Sterilized, the Carrier is a PVA Hydrogel

Experiment:

A 7% (m/v) solution of polyvinylalcohol (PVA, Sigma, 341584-25G) in water (heated to 85° C.) was prepared. The solution was cooled down to ambient temperature. Anti mouse IgG (biotinylated, Jackson ImmunoResearch, 115-065-003) was diluted to 200 µg/ml in PBS.

The hydrogel mixture was composed as follows:
6,75 ml PVA solution (7%)
4,5 µl anti mouse IgG (200 µg/ml)
2,25 either PBS or stabilizing solution (20 g/l albumin (Biotest Pharma) and 10 g/l mannitol (Serag Wiesner, 219675) in PBS)

PVA hydrogels were poured into small petri dishes (diameter 35 mm, 2 ml solution). The hydrogel films were air dried for 48 h. The samples were sterilized via beta irradiation (25 kGy) and unsterile controls were stored under cool conditions.

Assay:

An ELISA plate (Greiner Bio-one, 655061) was coated with the antigen (mouse IgG, Innovativ Research, Ir-Ms-Gf): the antigen was diluted to 1 µg/ml, 100 µl were pipetted to each well and incubated over night at 4° C. The plate was washed 2× with washing buffer (25× concentrate, Invitrogen, WB02). The plate was blocked with Albumin (5%) and washed again 3×.

The PVA hydrogels were placed in 6 well plates and covered with 2 ml PBS (without $Ca^{2+}/Mg^{2+}$, PAA, H15-002). After 30 min, 1 h and 2 h the PBS was collected and replaced with fresh PBS.

Serial dilutions of the samples and the standard were pipetted into the ELISA plate (2×200 µl each) and incubated for 1 h at ambient temperature. The plate was washed 3×. To each well 200 µl Streptavidin solution (Horseradish peroxidase (HRP) labeled, Pierce, 21126, diluted to 0.1 µg/ml in PBS) were added and incubated 1 h at ambient temperature. The plate was washed 3×. Chromogenic substrate TMB (TMB=tetramethylbenzidine, Invitrogen, 00-2023) was diluted 1:2 in $H_2O$ and 200 µl were added to each well. The plate was incubated 15 min at ambient temperature and was protected from light. To stop the color reaction 50 µl diluted $H_2SO_4$ (diluted 1:5 with aqua dest., Merck, 1007311000) were added. The absorption of the plate was detected at 450 nm (Fusion Photometer A153601, PerkinElmer).

Results:

The biomolecule (here an anti-mouse IgG antibody) loses most of its biological function during subsequent storage and or sterilisation (25 kGy irradiation) if no stabilizer is added. In contrast a stabilizer solution (Albumin and Mannitol) protected the biomolecule. The recovery of the eluted antibody is very high. Shown is the specific binding to the antigen.

EXAMPLE 6

Protective Effect of a Specific Amino Acid Composition 20 mg human anti-Hepatitis A antibody (Beriglobin (human IgG, AK), CSL Behring) and 40 mg of a protective composition were dissolved in water to a total volume of 525 µl per sample and lyophilized. Afterwards, the samples were dissolved in 1 ml water and tested for functionality using an HAV (Hepatitis A virus) IgG ELISA.

Composition:
20 g Arginine
20 g Histidine
20 g Lysine
3 g Glutamic acid
2 g Tryptophan
20 g Glycine
15 g Alanine
0.2 g Tween 80
1 g Glycyrrhizic acid ammonium salt The pH was adjusted to about 7.2 using NaOH and/or NaCl. Afterwards, the solutions were subjected to sterile filtration.

400 µl of solution (corresponding to 40 mg solid compounds) were mixed with 125 µl Beriglobin (corresponding to 20 mg antibody)

Lyophilisation:

Lyophilisation was carried out as follows:
initial freezing temperature −40° C.;
start of vacuum of 0.1 mBar after 3 h freezing time;
temperature rise of about 1.5° C./h for 23 h;
6 h drying over night at 6° C. and 0.004 mBar.

Sterilisation:

The lyophilized samples were irradiated with 25 kGy and one with 50 kGy Beta-radiation.

Figure 14:
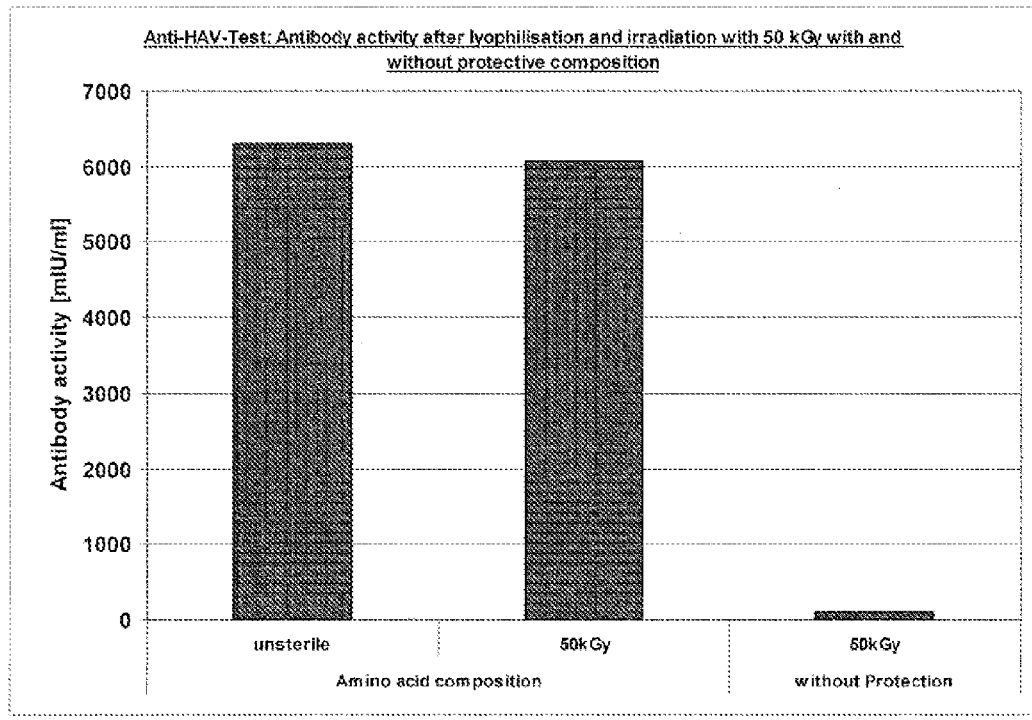

Results:

The results of the HAV-ELISA are depicted in FIG. 14.

After drying and sterilization white, non-odorant, inherently stable cakes were obtained. 1 ml water was added to each sample and the dissolution behaviour was monitored. Dissolution took place within less than 30 seconds and was free of aggregates. Even after 24 h neither macroscopic nor microscopic aggregation was detectable.

Conclusion:

Application of the composition resulted in only little loss of the Hepatitis A antibody portion of Beriglobin as compared to the not irradiated control.

EXAMPLE 7

Test of Different Saponins as Stabilizing Compounds. The Structural Class of Saponins has a Stabilizing Effect on Antibodies Materials & Methods All experiments were based on the same basic ELISA assay design. (see above)
Adsorption of LO-MM-3 to an ELISA plate and application of postcoatings
Stress exposure of the coated surface
ELISA detection of LO-MM-3 functionality Experiment:

Adsorption of LO-MM-3 to the plate and application of the postcoating and sterilization; as well as the general ELISA procedure were conducted as described in the Materials & Methods section. The irradiation dose (electron beam) was 50 kGy.

Figure 15:
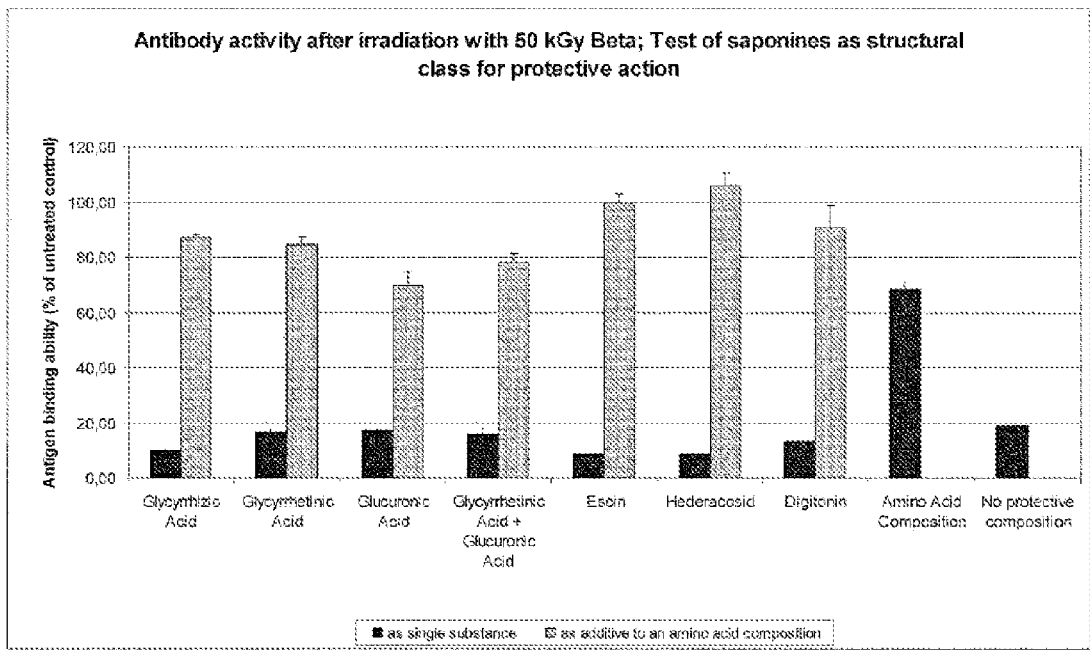

Results:

The results of the experiment are depicted in FIG. 15. The structural class of saponins has the potential to enhance the protective effect of amino acid combinations. Preferred is the use of the saponin glycyrrhizic acid.

EXAMPLE 8

Stabilizing Compositions Comprising at Least 3 Different Amino Acids or at Least Two Different Amino Acids and a Saponin such Glycyrrhizic Acid Provide Very Good Protection Materials & Methods All experiments were based on the same basic ELISA assay design. (see above)

Adsorption of LO-MM-3 to an ELISA plate and application of postcoatings

Stress exposure of the coated surface

ELISA detection of LO-MM-3 functionality

Experiment:

The amino acids were dissolved either in 0.5 M NaOH (Merck, 106482) or 0.5 M HCl (Merck, 100319) to obtain stock solutions with a maximal concentration. The amino acid stock solutions were mixed together in different combinations to get total amino acid concentrations of 20 g/l in the postcoating solutions.

The pH of the amino acid mixtures was set to approx. 7.0.

Adsorption of LO-MM-3 to the plate and application of the postcoating and sterilization; as well as the general ELISA procedure were conducted as described in the Materials & Methods section. The irradiation dose (electron beam) was 50 kGy.

Figure 16:
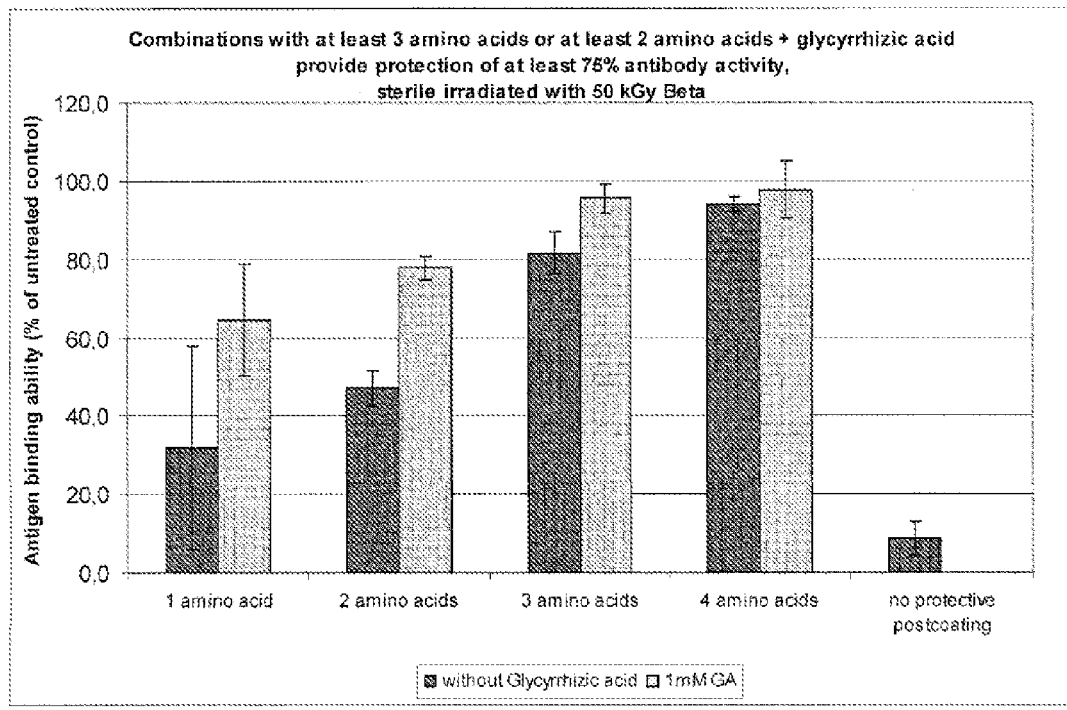

Results:

The results of the experiment are depicted in FIG. 16. Combinations of at least 3 amino acids and combinations of 2 amino acids with the addition of glycyrrhizic acid provide a maximal protection (more than 75%) of an immobilized antibody when sterilized with 50 kGy beta irradiation.

EXAMPLE 9

A Preferred Amino Acid Composition Provides Protection Under Different Stress Conditions Materials & Methods All experiments were based on the same basic ELISA assay design. (see above)

Adsorption of LO-MM-3 to an ELISA plate and application of postcoatings

Stress exposure of the coated surface

ELISA detection of LO-MM-3 functionality

Experiment:

Compositions used:

protective composition A (compound per liter)

20 g Arginine
20 g Histidine
20 g Lysine
3 g Glutamine
2 g Tryptophan
20 g Glycine
15 g Alanine
0.2 g Tween 80
1 g Glycyrrhizic acid ammonium salt The pH was adjusted to about 7.2 using NaOH and/or HCl. Afterwards, the solutions were subjected to sterile filtration.

Adsorption of LO-MM-3 to the plate and application of the postcoating and sterilization; as well as the general ELISA procedure were conducted as described in the Materials & Methods section.

Figure 17:
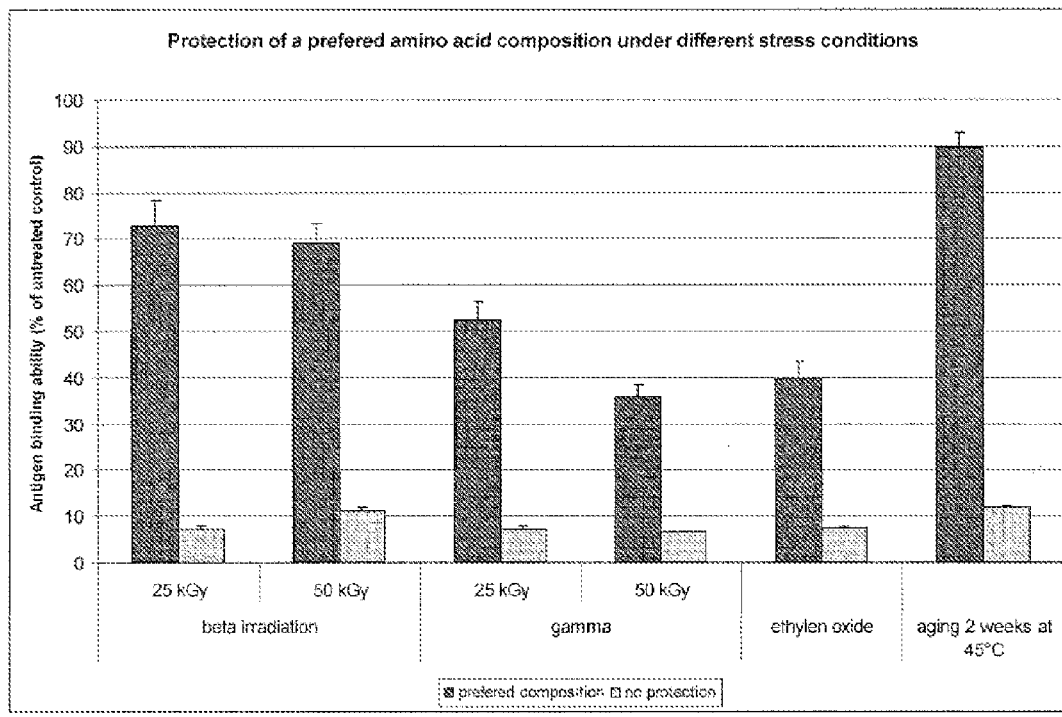

Results: The results of the experiment are depicted in FIG. 17. The amino acid composition provides protection under different stress conditions. The best protection is provided for beta irradiation with different doses and artificial aging under elevated temperature. The protection for gamma irradiation or ethylene oxide sterilisation is less but still relevant.

EXAMPLE 10

Amino Acid Postcoatings Provide Protection During Long-Time Storage

Experiment:

The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio.

18 amino acids: Ala, Arg, Asp, Gln, Glu, Gly, His, Ile, Leu, Lys, Met, Phe, Pro, Ser, Thr, Trp, Tyr, Val 5 amino acids (1): Asp, Arg, Phe, Ser, Val 5 amino acids (2): Ala, Glu, Lys, Thr, Trp 2 amino acids (1): Asp, Val 2 amino acids (2): Ala, Glu The pH of the amino acid mixtures was set to approx. 7.0; and the mixtures were further diluted in PBS to get the final concentration of 200 mM.

Adsorption of LO-MM-3 to the plate and application of the postcoating and sterilization; as well as the general ELISA procedure were conducted as described in the Materials & Methods section. Long-time storage was simulated by an accelerated aging procedure. The plates were stored at 45° C. and antibody activity was determined after 0, 10, 25, 41 and 62 days of storage. This equals real time aging at 5° C. of 0, 6, 12, 24 and 36 months.

Results:

Amino acid postcoatings containing at least 5 amino acids provide protection during longtime storage. For the non sterilized samples, after 62 days at 45° C. about 80% of the antigen binding ability is preserved. Sterilized samples (beta, 25 kGy) maintain about 70% of their antigen binding ability after 62 days at 45° C. Amino acid postcoatings containing only 2 amino acids maintain only about 40% antigen binding ability during the storage process, regardless of sterilization. The addition of 1 mM glycyrrhizic acid to the postcoating solutions enforces the protecting effect: For the non sterilized samples containing at least 5 amino acids and glycyrrhizic acid, after 62 days at 45° C. about 90% of the antigen binding ability is preserved. Sterilized samples (beta, 25 kGy) maintain about 80% of their antigen binding ability after 62 days at 45° C. Amino acid postcoatings containing 2 amino acids and glycyrrhizic acid maintain about 70% antigen binding ability during the storage process.

EXAMPLE 11

Amino Acid Postcoatings Provide Protection During Different Sterilization Processes Experiment:

The amino acids were dissolved either in 0.5 M NaOH (Merck, 106482) or 0.5 M HCl (Merck, 100319) to obtain stock solutions with a maximal concentration. The amino acid stock solutions were mixed together to get a total amino acid concentration of 200 mM in the postcoating solution. The amino acids were used in equimolar ratio.

18 amino acids: Ala, Arg, Asp, Gln, Glu, Gly, His, Ile, Leu, Lys, Met, Phe, Pro, Ser, Thr, Trp, Tyr, Val
5 amino acids: Asp, Arg, Phe, Ser, Val
2 amino acids: Asp, Val The pH of the amino acid mixtures was set to approx. 7.0; and the mixtures were further diluted in PBS to get the final concentration of 200 mM.

Adsorption of LO-MM-3 to the plate and application of the postcoating and sterilization; as well as the general ELISA procedure were conducted as described in the Materials & Methods section. One plate was irradiated (gamma, 25 kGy). The irradiation was conducted at Beta-Gamma-Service, Bruchsal, Germany. Another plate was sterilized by EO (ETO BO1 cycle); the sterilization was conducted at Rose GmbH, Trier, Germany.

Results:

Samples sterilized with gamma irradiation maintain about 85% activity when protected with an amino acid postcoating containing 18 amino acids; this effect is not further enhanced with glycyrrhizic acid; with 5 amino acids the remaining activity is 75%; with 2 amino acids only 40% are maintained. The protection with 2 amino acids is improved by the addition of glyccyrhizic acid; here the remaining activity is 65%. Samples sterilized with ETO maintain about 85% activity when protected with an amino acid postcoating containing 18 amino acids; this effect is not further enhanced with glycyrrhizic acid. Postcoatings containing 5 or 2 amino acids have only little protecting effect; the addition of glycyrrhizic acid enhances the protection marginally.

EXAMPLE 12

Postcoatings Consisting of Amino Acids and Dipeptides Provide Protection Against High Irradiation Doses Materials & Methods
All experiments were based on the same basic ELISA assay design. (see above)
Adsorption of LO-MM-3 to an ELISA plate and application of postcoatings
Stress exposure of the coated surface
ELISA detection of LO-MM-3 functionality
Experiment:

The amino acids were dissolved either in 0.5 M NaOH (Merck, 106482) or 0.5 M HCl (Merck, 100319) to obtain stock solutions with a maximum concentration. The amino acid stock solutions were mixed together to get a total amino acid concentration of 20 g/l in the postcoating solution. The dipeptides alone were used with a concentration of 10 g/l and in combination with amino acids with 2 g/l.

7 amino acids: Arg, His, Lys, Glu, Trp, Gly, Ala
2 dipeptides: Gly-Tyr, Gly-Gln

The pH of the amino acid mixtures was set to approx. 7.0.
Adsorption of LO-MM-3 to the plate and application of the postcoating and sterilization; as well as the general ELISA procedure were conducted as described in the Materials & Methods section. The irradiation dose (electron beam) was 50 kGy.

Results:

Samples sterilized with 50 kGy beta irradiation maintain about 60% activity when protected with an amino acid postcoating containing only 7 amino acids; this effect is further enhanced with the addition of dipeptides such as Gly-Tyr or dipeptide combinations. Glycyrrhizic Acid does not enhance the protective effect of the amino acid dipeptide combination further.

The invention claimed is:

1. A sterile container selected from vials, ampullas, cryo-containers, phials, flasks, bottles and bags, comprising
   a stabilizer composition acting as a carrier,
   at least one biomolecule selected from the group consisting of an antibody, enzyme, receptor, membrane protein, transport protein, blood coagulation factor, hormone, cytokine and function fragments of any of the foregoing, wherein the at least one biomolecule is reversibly attached to the carrier,
   and optionally
   a lid,
wherein the stabilizer composition
   partially or completely covers the attached biomolecules, and
   comprises at least three different naturally occurring amino acids, and wherein the at least three different naturally occurring amino acids are not in the form of peptides.

2. The container according to claim 1, wherein the at least one biomolecule is attached to the carrier such that it can be released from the carrier prior to use.

3. The container according to claim 1, wherein the carrier is solid.

4. The container according to claim 1, wherein the carrier is semi-solid.

5. The container according to claim 1, wherein the carrier is solubilizable.

6. The container according to claim 3, wherein the solid carrier is porous.

7. The container according to claim 5, wherein the solubilizable carrier comprises proteinaceous and/or carbohydrate structures that dissolve in aqueous, optionally buffered solutions.

8. The container according to claim 1, wherein the at least one stabilizer is comprised in a buffered solution.

9. The container according to claim 1, wherein the at least one stabilizer is a mixture of at least four different naturally occurring amino acids.

10. The container according to claim 1, wherein said mixture comprises at least one amino acid of each group of
   (a) an amino acid with nonpolar, aliphatic R groups;
   (b) an amino acid with polar, uncharged R groups;
   (c) an amino acid with positively charged R groups;
   (d) an amino acid with negatively charged R groups; and
   (e) an amino acid with aromatic R groups.

11. The container according to claim 9, wherein the amino acids comprised in said mixture are alanine, glutamic acid, lysine, threonine and tryptophan.

12. The container according to claim 9, wherein the amino acids comprised in said mixture are aspartate, arginine, phenylalanine, serine and valine.

13. The container of claim 1, wherein the container is a closable sterile container.

* * * * *